United States Patent [19]

Takehana et al.

[11] Patent Number: 4,977,886
[45] Date of Patent: Dec. 18, 1990

[54] POSITION CONTROLLING APPARATUS

[75] Inventors: Sakae Takehana; Koji Fujio, both of Hachioji; Yasuhiro Ueda, Kokubunji, all of Japan

[73] Assignee: Olympus Optical Co., Ltd., Tokyo, Japan

[21] Appl. No.: 428,144

[22] Filed: Oct. 27, 1989

[30] Foreign Application Priority Data

| Apr. 4, 1989 | [JP] | Japan | 1-085360 |
| Apr. 19, 1989 | [JP] | Japan | 1-099443 |
| Apr. 19, 1989 | [JP] | Japan | 1-208845 |
| May 17, 1989 | [JP] | Japan | 1-123758 |
| Jun. 4, 1989 | [JP] | Japan | 1-087257 |
| Aug. 2, 1989 | [JP] | Japan | 1-029284 |

[51] Int. Cl.$^5$ .................................. A61B 1/00
[52] U.S. Cl. .................................................. 128/4
[58] Field of Search ............................... 128/4, 45 M

[56] References Cited

U.S. PATENT DOCUMENTS 4,884,557 12/1989 Takahana et al. ............... 128/4 SM

FOREIGN PATENT DOCUMENTS 63-43765 9/1988 Japan .

Primary Examiner—William H. Grieb
Attorney, Agent, or Firm—Armstrong, Nikaido, Marmelstein, Kubovcik, & Murray

[57] ABSTRACT

The position controlling apparatus of this invention is to curve an endoscope insertable part or a catheter and is provided with an actuator having a shape memorizing alloy body. The shape memorizing alloy body is heated or cooled by a driving appartaus and the actuator is displaced by such heating or cooling. The difference between the actual displacement of the actuator driven by the driving apparatus and the objective displacement of the actuator is output by a comparing means which operates the driving apparatus on the basis of this difference. A resistance value detecting circuit detects the resistance value of the shape memorizing alloy body varying when the shape memorizing alloy body is heated or cooled. The detected value detected by the resistance value detecting circuit is input into a controlling apparatus which controls the driving apparatus on the basis of the detected value and the preset used temperature range of the shape memorizing alloy body.

34 Claims, 33 Drawing Sheets

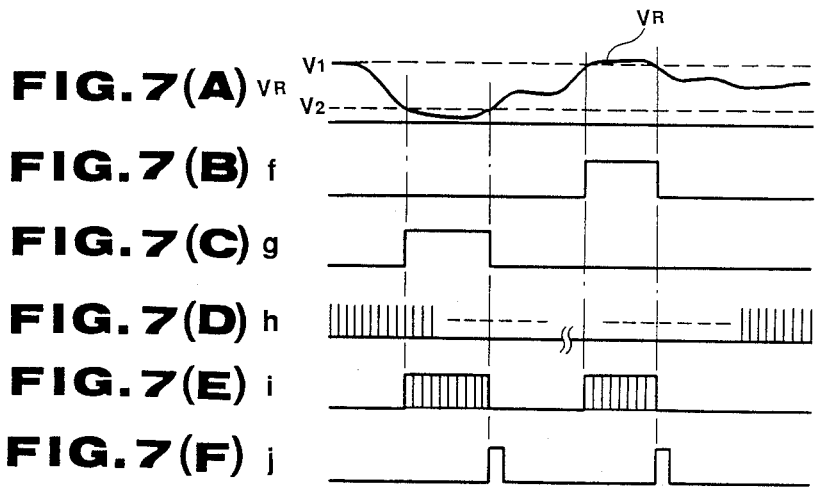
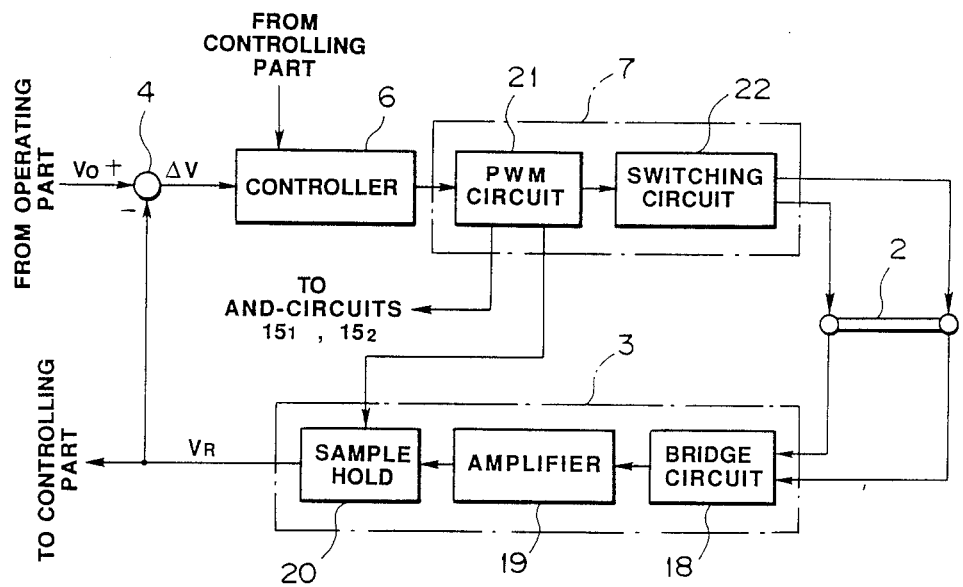

FIG.15
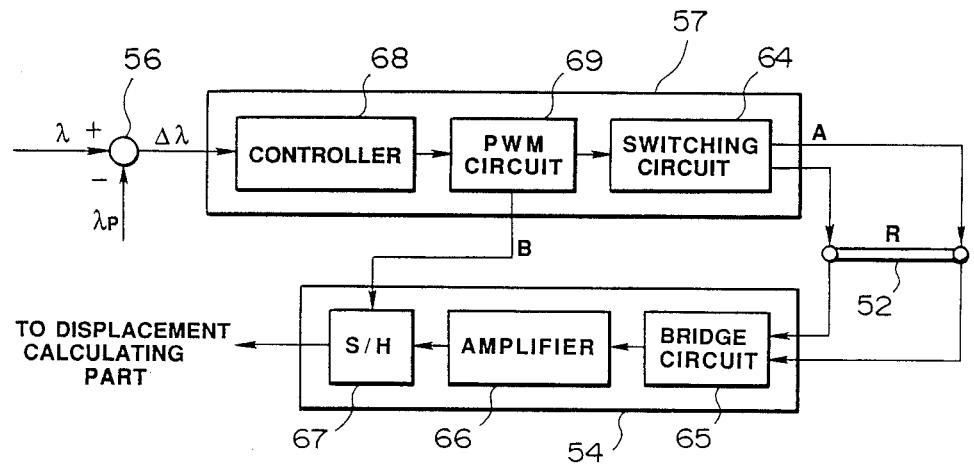
FIG. 16(a) DRIVING PULSE A 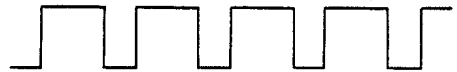
FIG. 16(b) SAMPLING PULSE B 

FIG. 21
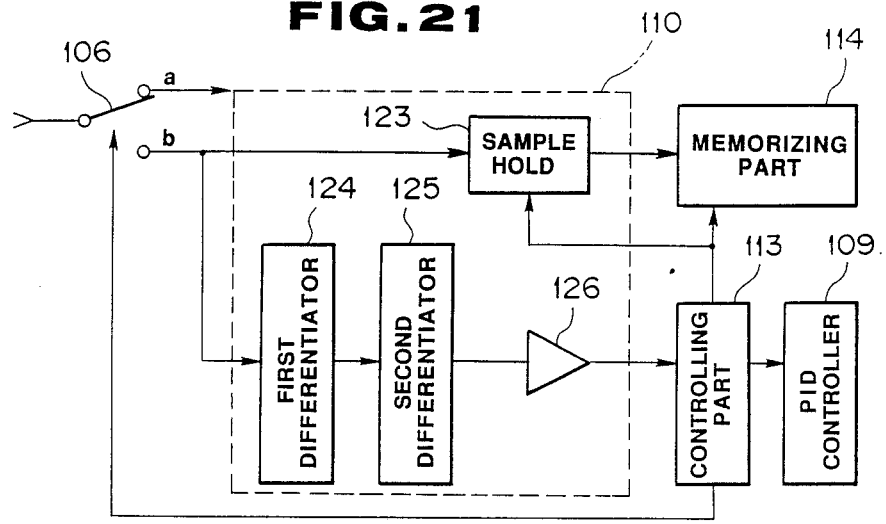
FIG. 22(a) OUTPUT OF RESISTANCE DETECTING PART
FIG. 22(b) OUTPUT OF FIRST DIFFERENTIATOR
FIG. 22(c) OUTPUT OF SECOND DIFFERENTIATOR
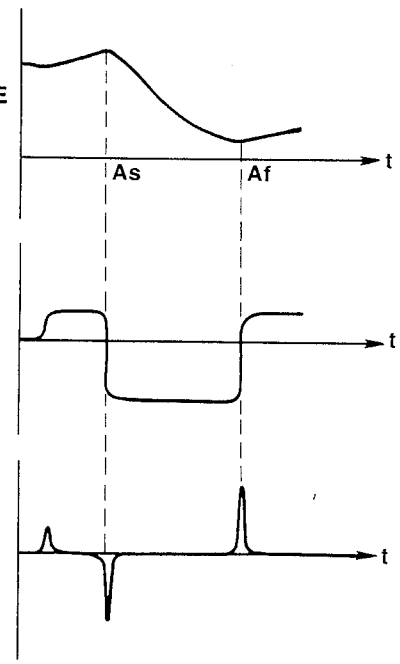

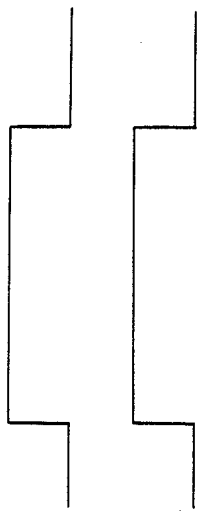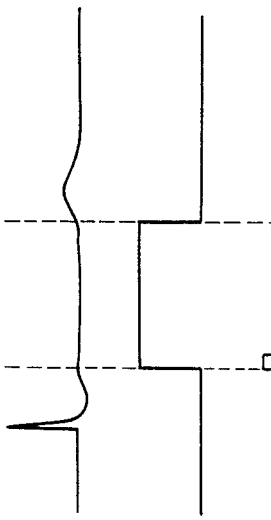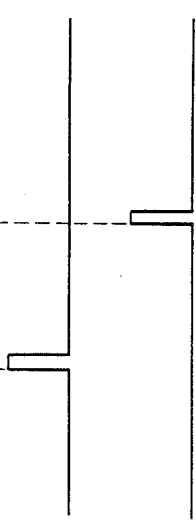

FIG.35(a) ELECTRIFICATION CONTROLLING PART INITIAL ELECTRIFYING SIGNAL

FIG.35(b) ELECTRIFYING CIRCUIT OUTPUT ELECTRIFYING CURRENT

FIG.35(c) RESISTANCE VALUE DETECTING PART OUTPUT SIGNAL

FIG.35(d) DIFFERENTIATING CIRCUIT OUTPUT SIGNAL

FIG.35(e) COMPARING CIRCUIT (a) OUTPUT SIGNAL

FIG.35(f) TRIGGER SIGNAL GENERATING CIRCUIT (a) OUTPUT SIGNAL

FIG.35(g) TRIGGER SIGNAL GENERATING CIRCUIT (b) OUTPUT SIGNAL

POSITION CONTROLLING APPARATUS

FIELD AND BACKGROUND OF THE INVENTION:

This invention relates to a position controlling apparatus adapted to control the position of an actuator using a shape memorizing alloy.

To control an actuator using a shape memorizing alloy body, there is already known a method of controlling about actuator with an information about the position of the actuator, the force applied to the actuator or the temperature by providing the actuator with a position detecting apparatus such as a potentiometer, a force detecting apparatus or temperature detecting apparatus.

In the conventional method of detecting the position or force of an actuator, the state of the actuator can be detected but the state of a shape memorizing alloy body which is a driving source, that is, the temperature of the shape memorizing alloy body can not be detected and therefore no judged whether the shape memorizing alloy is in a normal operating range or not.

In a method of detecting the temperature of a shape memorizing alloy body, a temperature sensor such as a thermistor is used but it is so difficult to make the sensor closely adhere to the shape memorizing alloy that the temperature of the shape memorizing alloy body can not be always correctly detected.

Therefore, with the conventional technique, the shape memorizing alloy is likely to be overheated and will deteriorate during recovering of the memorized shape and, when the alloy is further overheated, the memorized shape will be lost and the other parts forming the actuator will be damaged. When the shape memorizing alloy is overcooled, its fatigue will become so large that the characteristics will likely be deteriorated (such as in reduction in the lifespan.).

A position controlling apparatus effective to realize an actuator which is so small that a position detecting apparatus or the like can not be added to the outside in particular is shown, for example, in the publication of Japanese patent application laid open No. 33612/1985 and is characterized by detecting information relating to the displacement of the actuator by respective information about the resistance value of a shape memorizing alloy forming the actuator and the force applied to the actuator.

Now, in the article "Development of a Shape Memorizing Alloy Actuator" in Japan Robot Institute Journal, Vol. 4 No. 2 (April, 1986), in order to make it easy to handle a resistance value variation as a measure of a cotransformation rate, a normalized resistance value $\lambda$ is introduced. The normalized resistance value $\lambda$ is defined by the following formula where the maximum value of the resistance value R of a shape memorizing alloy body is represented by R max and the minimum value thereof is represented by R min $$\lambda = \frac{R\ max - R}{R\ max - R\ min}$$

wherein R max > R min.

That is to say, the normalized resistance value $\lambda$ is an index showing the rate of the mother phase occupied in the total phase so that, when shape memorizing alloys are competitively arranged and the respective normalized resistance values $\lambda$ are represented by $\lambda_1$ and $\lambda_2$, while satisfying the relation of $\lambda_1 + \lambda_2 = 1$, the resistance values may be varied may be cooperatively controlled and may be favorably controlled by the reduction of the hysteresis.

However, in this conventional example, as the resistance value of the shape memorizing body is determined and the displacement of the actuator is determined by the resistance value, the following problems will be produced. That is to say, the resistance value of the shape memorizing alloy body will be low in reproductivity and will delicately vary due to the environment and fatigue. Therefore, in case the resistance value and displacement are made to correspond to each other, an error will be produced and no favorable control will be obtained.

OBJECT AND SUMMARY OF THE INVENTION:

An object of the present invention is to prevent the overheating of a shape memorizing alloy body by interrupting or reducing the heating of the shape memorizing alloy in case the shape memorizing alloy body memorizing alloy in case the shape memorizing alloy body deviates from a normal operating range.

Another object of the present invention is to prevent the overcooling of a shape memorizing alloy body by interrupting or reducing the cooling of the shape memorizing alloy body in case the shape memorizing alloy body deviates from a normal operating range.

A further object of the present invention is to provide a position controlling apparatus whereby, even in case the resistance value of the shape memorizing alloy body is fluctuated by the environment or fatigue, the resistance value fluctuation will be automatically compensated and a favorable position control will be always possible at a high precision.

The position controlling apparatus of the present invention comprises an actuator having a shape memorizing alloy body as a power source a driving apparatus heats and cools the above mentioned shape memorizing alloy body and displaces the actuator by the heating and cooling. A comparing device outputs the difference between the actual displacement of the actuator driven by the driving apparatus and the objective displacement of the actuator and operating the driving apparatus on the basis of this difference. A resistance value detecting circuit detects a resistance value of the shape memorizing alloy body varying when the shape memorizing alloy body is heated or cooled. A controlling apparatus inputs the detected value detected by the resistance value detecting circuit and controls the driving apparatus on the basis of this detected value and the preset used temperature range of the shape memorizing alloy body.

According to the position controlling apparatus of the present invention, when the state of the shape memorizing alloy body is detected by its resistance value and the shape memorizing alloy body is overheated or overcooled, the shape memorizing alloy body driving apparatus will be controlled to interrupt or reduce the heating or cooling and therefore the overheating and overcooling of the shape memorizing alloy body can be positively prevented. Therefore, the shape memorizing alloy body can be prevented from losing the memorized shape or deteriorating the shape recovering characteristics.

BRIEF DESCRIPTION OF THE DRAWINGS:

FIGS. 3(a)-3(f) show signal waveform diagrams of essential parts for explaining the operation of FIG. 2.

FIGS. 7(A)-7(F) show signal waveform diagrams of essential parts for explaining the operation of FIG. 6.

FIG. 8 shows formation diagrams of a resistance detecting part and driving part in the fourth embodiment.

FIGS. 13 to 15 are formation diagrams for explaining in detail a resistance detecting part and driving part in the sixth embodiment.

FIGS. 16(a)-(b) shows pulse waveform diagrams for explaining the operation of FIG. 15.

FIGS. 20 and 21 are formation views for explaining in detail a resistance variation width detecting part in the eighth embodiment.

FIGS. 22(a)-22(c) show signal waveform diagrams of essential parts for explaining the operation of FIG. 21.

FIG. 31 is a sectioned view of a curvable part of the endoscope.

FIG. 32 is a diagram showing the relation between the temperature and resistance value of the shape memorizing alloy body.

FIGS. 33 to 37 relate to the 12th embodiment of the present invention.

FIG. 33 is a schematic formation diagram of the system.

FIG. 34 is a block diagram of a resistance value linearly varying part detecting circuit.

FIGS. 35(a)-35(g) waveform diagrams for explaining a part of the operation of the resistance value linearly varying part detecting circuit.

FIG. 36 is a block diagram of a logarithm-index converting part.

FIG. 37 is a characteristic diagram of the variation of the electric resistance value with the temperature variation of a driving member.

FIG. 38 is a block diagram of a light source apparatus.

FIG. 39 is a waveform diagram of the voltage fed to a driving member.

FIG. 41 is a perspective view of an entire catheter.

FIG. 42 is a sectioned side view in the vicinity of the catheter tip part.

FIG. 43 is a sectioned side view of the hand base side part of the catheter.

FIGS. 44 to 46 are explanatory views of the using state.

FIG. 47 is a side view of the tip part of an insertable part as disassembled.

FIG. 48 is a sectioned view on line II - II in FIG. 47.

FIG. 49 is a side view of the same as assembled.

FIG. 50 is a side view of the tip part of an insertable part as disassembled.

FIG. 51 is a sectioned view on line V - V in FIG. 50.

FIG. 52 is a side view of the same as assembled.

FIG. 53 is a side view of the tip part of an insertable part as disassembled.

FIG. 54 is a side view of a part of a curvable unit.

FIG. 55 is a sectioned view on line IX - IX in FIG. 53.

DETAILED DESCRIPTION OF THE PREFERRED EMBODIMENTS OF THE INVENTION:

The embodiments of the present invention shall be explained in the following with reference to the drawings.

Figure 1:
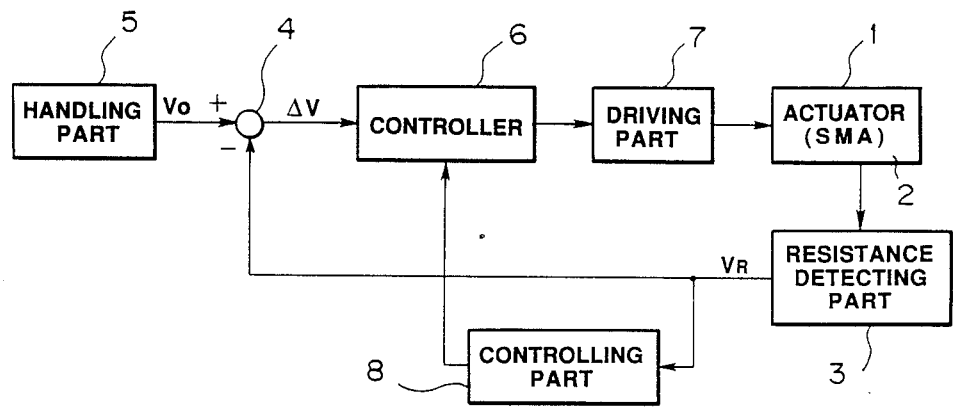
FIG. 1 is a formation diagram showing the first embodiment.

FIG. 1 shows the first embodiment of the present invention. That is to say, an actuator 1 is made of shape memorizing alloy body (SMA) 2 as, for example, of Ni-Ti. A resistance detecting part (resistance detecting means) 3 is electrically connected to the shape memorizing alloy body 2 to detect a resistance value R of the shape memorizing alloy body 2 and to output a resistance value signal $V_R$.

A comparator (comparating means) 4 compares the resistance value signal $V_R$ output from the resistance detecting part 3 with a reference signal $V_O$ output from a handling part 5 to output a difference signal $\Delta V$ between them.

A controller 6 receives the difference signal output from the comparator 4 and outputs a control signal in response to the difference signal $\Delta V$. A driving part (driving means) 7 receives the control signal output from the controller 6 and electrifies and heats the shape memorizing alloy body 2 with an electric current proportional to the control signal to drive the actuator 1.

When the actuator 1 is driven, the resistance value of the shape memorizing alloy body 2 will vary, the resistance value signal $V_R$ will move to a value close to the reference signal $V_O$ and the difference signal $\Delta V$ output from the comparator 4 will become small. As a result, the actuator 1 will operate in proportion to the reference signal $V_O$.

Also, the resistance value signal $V_R$ output from the resistance detecting part 3 will be input into a controlling part 8 and, when the shape memorizing alloy body 2 is overheated or overcooled, a control signal will be output to the controller 6.

Figure 4:
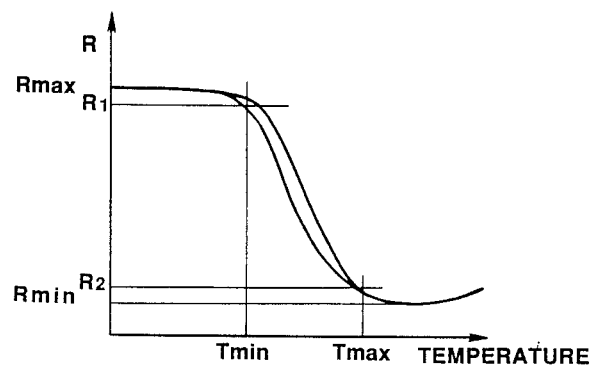
FIG. 4 is a diagram showing the relation between the temperature and resistance value of a shape memorizing alloy body.

The relation between the temperature and resistance value of the shape memorizing alloy body 2 is shown in FIG. 4. Usually, the shape memorizing alloy body 2 is used in a temperature range from T min to T max and then the resistance value of the shape memorizing alloy body 2 will vary in the range from R max to R min. When the shape memorizing alloy body 2 is heated (overheated) for a long time above the temperature T max, it will lose its memorized shape. When the shape memorizing alloy body 2 is heated (overcooled) for a long time below the temperature T min, the fatigue characteristics will deteriorate and will have a short lifespan.

Therefore, in this embodiment, control of the alloy is done by using the resistance value of the shape memorizing alloy body 2, therefore, the overheating or overcooling of the shape memorizing alloy body 2 is determined in the controlling part 8 by using the resistance value to control the driving part 7 with the controller 6.

Figure 2:
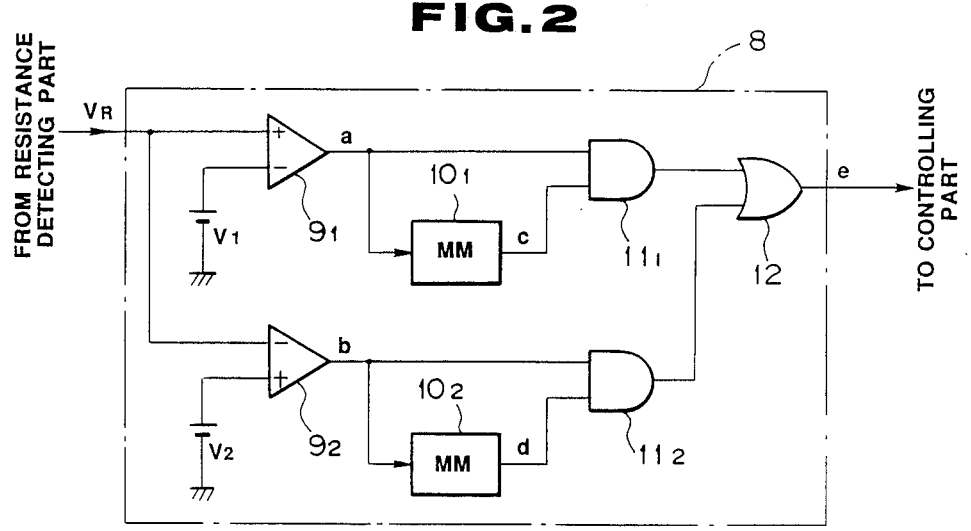
FIG. 2 is a formation diagram of a controlling part in the first embodiment.

The controlling part 8 shall be explained in detail in the following with reference to FIGS. 2 and 3. The resistance value signal $V_R$ output from the resistance detecting part 3 is input into one input end of each of comparators $9_1$ and $9_2$. Voltages $V_1$ and $V_2$ corresponding to the resistance values $R_1$ and $R_2$ of the shape memorizing alloy body 2 are input as reference voltages to the other input ends of the comparators $9_1$ and $9_2$. As shown in FIG. 4, the resistance value $R_1$ is somewhat smaller than R max and the resistance value $R_2$ is somewhat larger than R min and either value may be determined in consideration of safety.

The respective outputs a and b of the comparators $9_1$ and $9_2$ are input respectively into the respective input ends of monostable multivibrator circuits (abbreviated merely as MM circuits hereinafter) $10_1$ and $10_2$ and AND circuits $11_1$ and $11_2$. The respective outputs c and d of the MM circuits $10_1$ and $10_2$ are input respectively into the respective other input ends of the AND circuits $11_1$ and $11_2$. The respective outputs of the AND circuits $11_1$ and $11_2$ are input into an OR circuit 12 and the output e of this OR circuit 12 is delivered as a control signal to the controller 6.

Figure 3A:
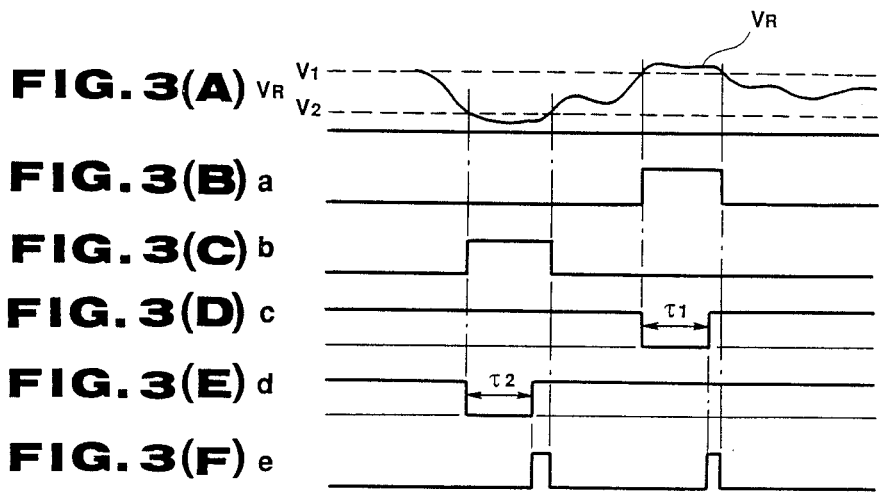

When the shape memorizing alloy body 2 is heated, its resistance value R will reduce and accordingly the resistance value signal $V_R$ output from the resistance detecting part 3 will reduce as shown in FIG. 3. When it is further continued to be heated, the resistance value signal $V_R$ will become smaller than the voltage $V_2$. At this time, the output b of the comparator $9_2$ will vary from a low level to a high level from the low level. By the rise of this signal b, the MM circuit $10_2$ will be triggered and, as shown in FIG. 3, a pulse d of a predetermined pulse width $\tau_2$ will be generated. The above mentioned pulse width is set to be the longest time for which, even if the shape memorizing alloy body 2 is continued to be heated, the memorized shape will not be lost.

Then, the logical product of the signals b and d of the AND circuit $11_2$ is taken. If the time when the resistance value signal $V_R$ is lower than the voltage $V_2$ (overheating state) is longer than the above mentioned pulse width $\tau_2$, the AND circuit $11_2$ will output a pulse. This pulse will become a control signal e through the OR circuit 12 and the control signal e will be input into the controller 6 to act to stop the heating operation of the driving part 7.

When the heating operation of the driving part is stopped, the shape memorizing alloy body 2 will be cooled and therefore the resistance value signal $V_R$ will begin to rise as shown in FIG. 3. When further cooled, the resistance value signal $V_R$ will exceed the voltage $V_1$. In this case, too, by the same operation as is mentioned above, the cooling of the shape memorizing alloy body 2 will be stopped and the resistance value signal $V_R$ will be controlled to be within the range of the voltages $V_1$ to $V_2$.

By the above series of operations, the overheating or overcooling of the shape memorizing alloy body 2 can be positively prevented.

In the above mentioned embodiment, the electrifying heating is used to heat the shape memorizing alloy body 2 but, for example, a heater or light may be also be used.

Also, it is apparent that air or water may be fed to cool the shape memorizing alloy body 2 or a Peltier element may be used to heat and cool it.

In order to obtain a pulse of a predetermined pulse width, the MM circuit is used but, for example, a timer circuit or the like may be used.

Further, by using a so-called PID controller for the controller 6, from the response in the case of determining the maximum value and minimum value of the resistance value of the shape memorizing alloy body 2, parameters (a proportional gain, integrating time and differentiating time) may be automatically tuned.

Figure 5:
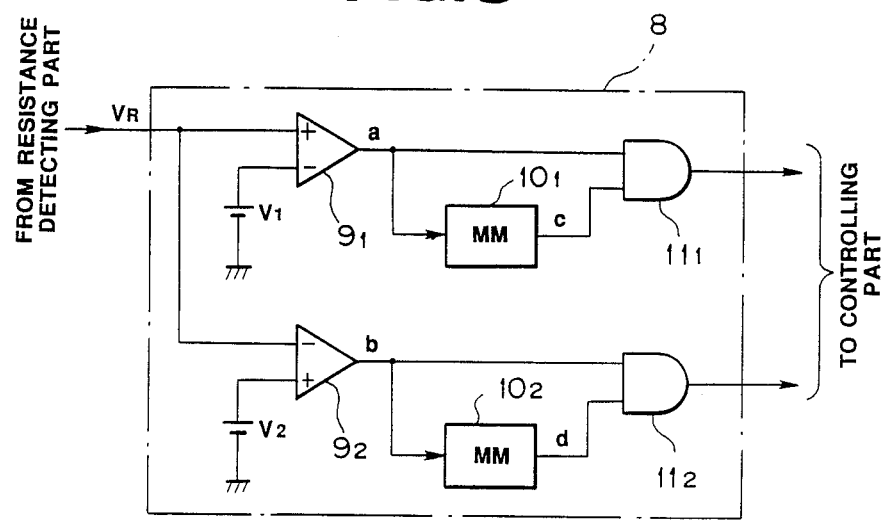
FIG. 5 is a formation diagram of a controlling part in the second embodiment.

FIG. 5 shows the second embodiment of the present invention. The parts other than the controlling part 8 are the same as in the first embodiment and are therefore omitted. This embodiment is a modification of the first embodiment and has the OR circuit 12 omitted so that the outputs of the AND circuits $11_1$ and $11_2$ may be input directly into the controller 6. In this case, the heating operation of the driving part 7 will be stopped by the output signal of the AND circuit $11_2$ and the cooling operation of the driving part 7 will be stopped by the output signal of the AND circuit $11_1$.

Figure 6:
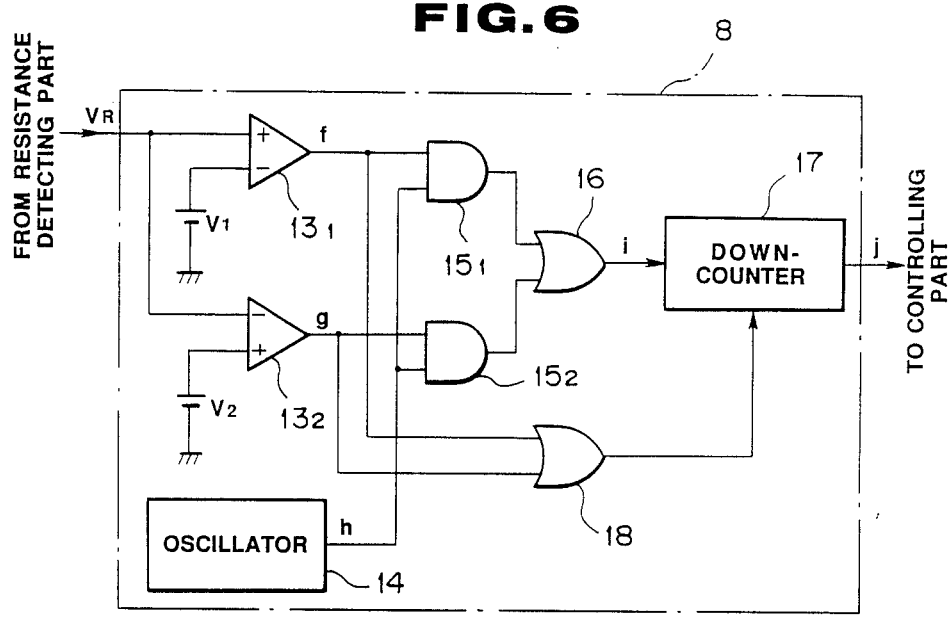
FIG. 6 is a formation diagram of a controlling part in the third embodiment.

FIG. 6 shows the third embodiment of the present invention. The parts other than the controlling part 8 are the same as in the first embodiment and are therefore omitted. In the controlling part 8, the resistance value signal $V_R$ output from the resistance detecting part 3 is input into one input end of each the comparators $13_1$ and $13_2$. Reference voltages $V_1$ and $V_2$ are fed respectively to the other input ends of the comparators $13_1$ and $13_2$. From the respective outputs of the comparators $13_1$ and $13_2$, pulses f and $g_1$ as are shown in FIG. $7_1$ will be obtained from the value of the resistance value signal $V_R$.

When the respective logical products of the pulses f and g and the pulse h of the frequency F (Hz) output from an oscillator 14 are taken respectively in the AND circuits $15_1$ and $15_2$ and the respective outputs are input into an OR circuit 16, a signal i as is shown in FIG. 7 will be obtained from the output.

A down-counter 17 is loaded with a preset numerical value n and counts down the pulse i output from the OR circuit 16. At this time, the down-counter 17 will be controlled in the counting operation by the output of an OR circuit 18 taking the logical sum of the respective outputs f and g of the comparators $13_1$ and $13_2$. When the counts of the down-counter 17 exceed the numerical value n, the down-counter 17 will output a control signal j. When this control signal j is fed to the controller 6, the driving part 7 will be controlled the same as in the first embodiment.

The numerical value n set in the down-counter 17 is set, for example, as follows. When the longest time for which, even if the shape memorizing alloy body 2 is continuously heated, the memorized shape will not be lost is represented by T, from the oscillating frequency F of an oscillator 14, [n=T×F] may be made.

FIG. 8 shows the fourth embodiment of the present invention. In this embodiment, the resistance detecting part 3 comprises a resistance bridge circuit 18, an amplifier 19 and a sampling-holding circuit (S/H) 20, the driving part 7 comprises a PWM (pulse width modulated) circuit 21 and a switching circuit 22 and the pulse used in the PWM circuit 21 is used instead of the output h of the oscillator 14 within the controlling part 8 in the third embodiment in FIG. 6.

That is to say, the shape memorizing alloy body 2 is driven to be modified by the driving pulse output from the switching circuit 22 and is electrically connected to the bridge circuit 18 from which is output a signal corresponding to the resistance value of the shape memorizing alloy body 2. The output signal of the bridge circuit 18 is amplified by the amplifier 19 and is then fed to the sampling-holding circuit 20 which sample-holds the output signal of the amplifier 19 by the sampling pulse output in the off-period of the driving pulse from the PWM circuit 21. The sample-held signal is input into the comparator 4 as a resistance value signal $V_R$. Further, a difference signal ΔV is calculated in the comparator 4 and is fed back to the controller 6. The signal from the controller 6 is input into the PWM circuit 21. By controlling the switching circuit 22 with this PWM circuit 21, the pulse width of the driving pulse is variably controlled in the direction making the difference signal ΔV smaller and the shape memorizing alloy body 2 is driven by the switching circuit 22.

A pulse of a predetermined frequency is output from the PWM circuit 21 and is input into the AND circuits $15_1$ and $15_2$ of the controlling part 8. In this case, when the frequency of the above mentioned pulse is represented by F', the numerical value n' set in the down-counter 17 will be [n'=T×F'].

According to the above mentioned fourth embodiment, as there is no need of specifically providing the oscillator 14, the circuit formation of the controlling part 8 is simple.

Figure 9:
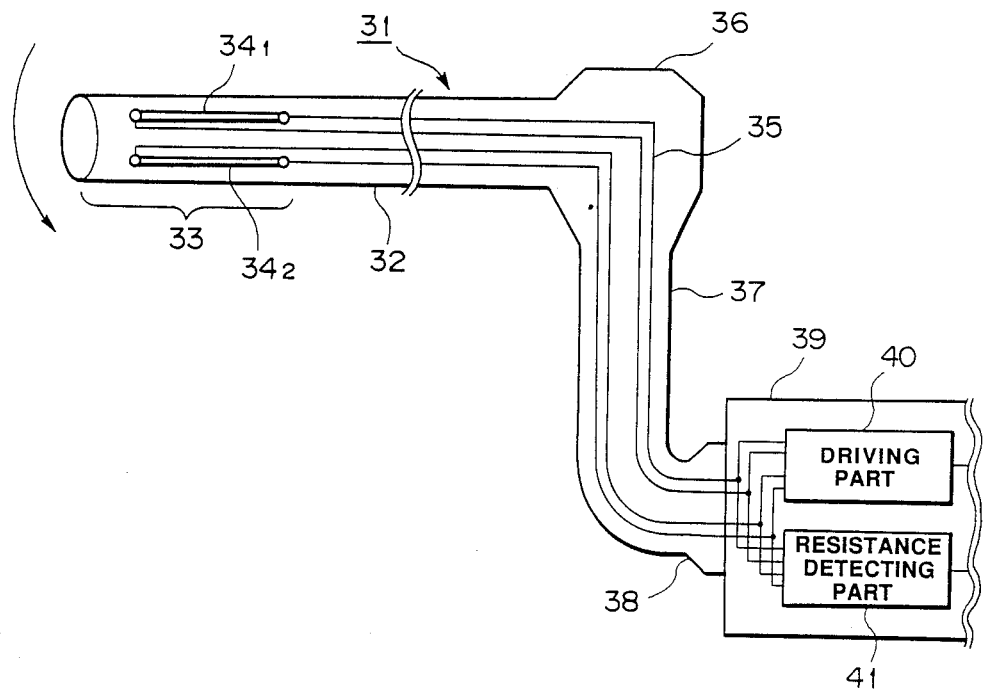
FIG. 9 is a formation diagram showing the fifth embodiment.

FIG. 9 shows the fifth embodiment of the present invention. This embodiment is shown as applied, for example, to an endoscope. That is to say, an endoscope 31 is provided at the tip of the insertable part 32 with a curved part 33 within which a pair of shape memorizing alloy bodies $34_1$ and $34_2$ are provided. Lead wires 35 are connected to the shape memorizing alloy bodies $34_1$ and $34_2$, are inserted through an operating part 36 and universal cord 37 and are led to a light source apparatus 39 through a connector 38. Parts the same as the respective parts shown in FIG. 11 as a driving part 40 and resistance detecting part 41 are provided within the light source apparatus 39.

Figure 10:
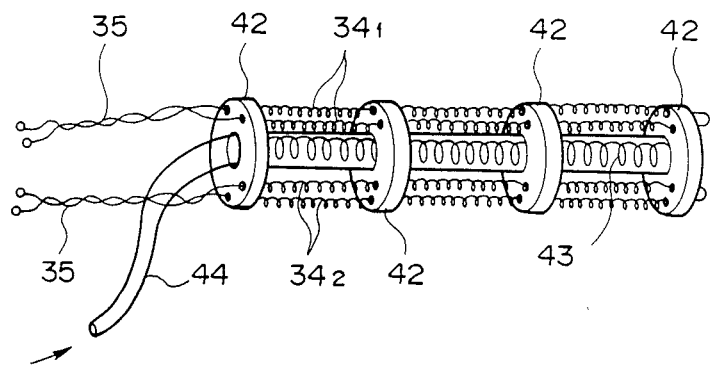
FIG. 10 is a perspective view for explaining the structure within a curvable part in FIG. 9.

In the structure within the curvable part 33, as shown, for example, in FIG. 10, a pair of shape memorizing alloy bodies $34_1$ and $34_2$ are fixed to a plurality of flanges 42 which are provided in the central parts with a bias spring 43 in the axial direction and are also provided on the center axis with a cooling tube 44 through which air is fed in to cool the shape memorizing alloy bodies $34_1$ and $34_2$.

Figure 11:
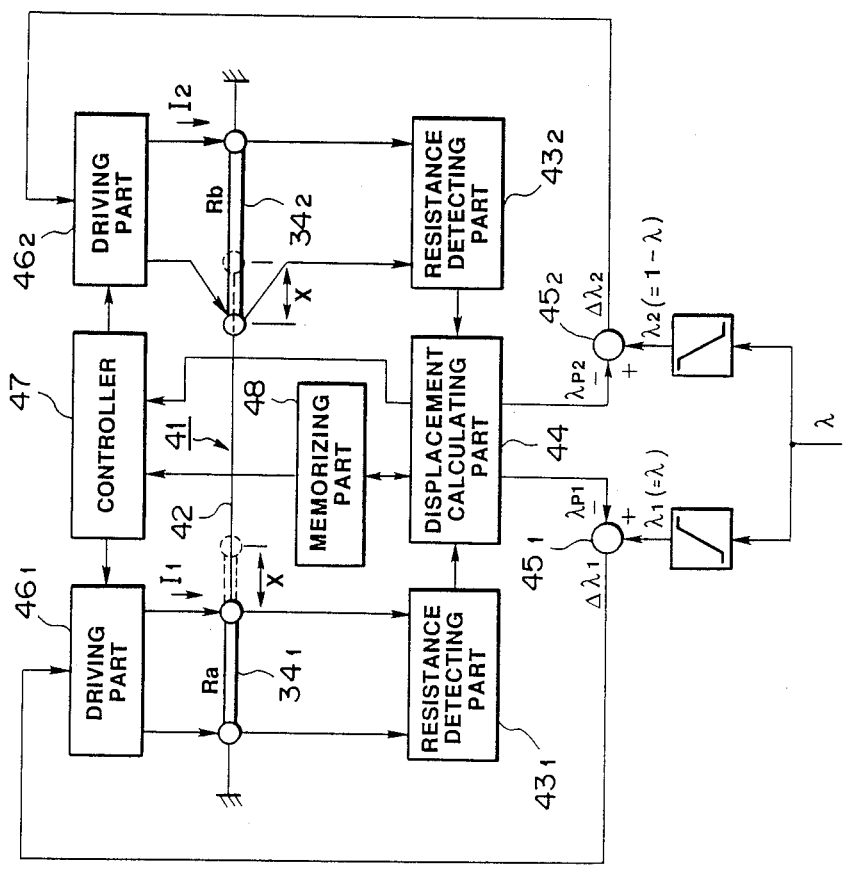
FIG. 11 is a block diagram of an endoscope in FIG. 9.

FIG. 11 shows a block diagram of the endoscope 31 shown in FIG. 9. An actuator 41 (corresponding to the curvable part 33 of the endoscope 31) comprises a shape memorizing alloy bodies $34_1$ and $34_2$ as, for example, of Ni-Ti and a connecting part 42 connecting them. In FIG. 11, the shape memorizing alloy body $34_1$ is shown to be in a high temperature state and the shape memorizing alloy body $34_2$ is shown to be in a low temperature state. When the shape memorizing allow body $34_1$ is at a low temperature and the shape memorizing alloy body $34_2$ is at a high temperature, they will be as shown by the broken lines.

Resistance detecting parts $43_1$ and $43_2$ are electrically connected respectively to the shape memorizing alloy bodies $34_1$ and $34_2$ to detect resistance values Ra and Rb of the shape memorizing alloy bodies $34_1$ and $34_2$ and to output resistance value signals.

A displacement calculating part 44 receives the resistance value signals output from the resistance detecting part $43_1$ and $43_2$, calculates a displacement x of the actuator 41 on the basis of the respective resistance signals and outputs displacement signals $\lambda_{P1}$ and $\lambda_{P2}$.

Comparators $45_1$ and $45_2$ compare respectively the displacement signals $\lambda_{P1}$ and with reference signals $\lambda_1$ and $\lambda_2$ to calculate difference signals $\Delta\lambda_1$ and $\Delta\lambda_2$.

Driving parts $46_1$ and $46_2$ receive the difference signals $\Delta\lambda_1$ and $\Delta\lambda_2$ electrify and heat the shape memorizing alloy bodies $34_1$ and $34_2$ respectively with electric currents $I_1$ and $I_2$ to drive the actuator 41.

When the actuator 41 is driven, the displacement signals $\lambda_{P1}$ and $\lambda_{P2}$ output from the displacement calculating part 44 will shift respectively to values close to the reference signals $\lambda_1$ and $\lambda_2$ and the difference signals $\Delta\lambda_1$ and $\Delta\lambda_2$ output from the comparators $45_1$ and $45_2$ will become small enough. As a result, the displacement x of the actuator 41 will be held proportional to the values of the reference signals $\lambda_1$ and $\lambda_2$.

Into a controller 47 are input the maximum value R max and minimum value R min of the resistance values of the shape memorizing alloy bodies $34_1$ and $34_2$ from a memorizing part. Also input are the respective resistance values of the shape memorizing alloy bodies $34_1$ and $34_2$ from the displacement calculating part 44 so that the controller 47 may output a control signal stopping the driving parts $46_1$ and $46_2$ on the basis of the respective input data.

The normalized resistance value λ shows the rate of the mother phase occupied in the entire phase and there is a substantially linear relation between the normalized resistance value λ and the generating force or displacement. Therefore, by making the normalized resistance value λ an objective value, the displacement (position) of the actuator 41 can be controlled.

However, as the resistance value of the shape memorizing alloy body varies generally with the environment and fatigue, with conventional practice the maximum value R max and minimum value R min of the resistance values of the shape memorizing alloy body are determined in advance and are converted to the normalized resistance value λ which can not be said to correctly show the rate of the mother phase and can not further precisely control the displacement (position).

Therefore, in this embodiment, just before driving the actuator 41, the maximum value R max and minimum value R min of the respective resistance values Ra and Rb of the shape memorizing alloy bodies $34_1$ and $34_2$ are respectively detected and can be stored in the memorizing part 48.

For example, before being electrified and heated by the driving parts $46_1$ and $46_2$, the shape memorizing alloy bodies $34_1$ and $34_2$ are well cooled, the respective resistance values then of the shape memorizing alloy bodies $34_1$ and $34_2$ are detected with the resistance detecting parts $43_1$ and $43_2$ and the detected values are made the maximum values R max. Then, electric currents $I_1$ and $I_2$ sufficient to transform the shape memorizing alloy bodies $34_1$ and $34_2$ are fed respectively from the driving parts $46_1$ and $46_2$ and, after the lapse of a time sufficient to end the transformation, the respective resistance values of the shape memorizing alloy bodies $34_1$ and $34_2$ are detected the same as is mentioned above and the detected values are made the minimum values R min. The thus determined maximum values R max and minimum values R min are stored in the memorizing part 48 through the displacement calculating part 44 so that, by determining the normalized resistance value λ in the displacement calculating part 44 on the basis of these respective values, the correct mother phase rate may be shown and the displacement (position) of the actuator 41 may be precisely controlled.

The controller 47 reads the maximum values R max and minimum values R max of the resistance values out of the memorizing part 48, calculates the resistance values $R_1$ and $R_2$ on the basis of those respective values and can prevent the overheating and overcooling of the shape memorizing alloy bodies $34_1$ and $34_2$. In this case, as the reference voltage of the controller 47 correctly reflects the resistance value varying range (R max and R min), the overheating and overcooling can be prevented more precisely and positively.

In the conventional endoscope, it has been very difficult to obtain a desired curvature correctly and easily but, in this embodiment, by detecting and feeding back the resistance values of the shape memorizing alloy bodies $34_1$ and $34_2$, any desired curvature can be correctly and easily obtained.

In case the apparatus is applied to an endoscope, it will be necessary to make the apparatus small, it will be difficult to use a position sensor or the like and a position control using the resistance value of a shape memorizing alloy body will be adapted.

It is apparent that, in the above mentioned embodiment, the shape memorizing alloy bodies $34_1$ and $34_2$ may be coil spring-like, linear or plate-like.

It is also apparent that the displacement calculating part 44, controller 47 and memorizing part 48 may be formed of software, for example, by microcomputers.

Each of the shape memorizing alloy bodies $34_1$ and $34_2$ is turned back at the end flange 42 to be reciprocated but need not be reciprocated in particular and may be determined in response to the generated force and dimensions.

Also, a pair of shape memorizing alloy bodies are provided to make a two-direction curvable type endoscope 31 but, for example, two pairs of shape memorizing alloy bodies may be provided to make a four-direction curvable type endoscope 31.

By providing in series a plurality of the curvable parts 33 shown in FIG. 9, a multi-articulated endoscope 31 can be realized.

The endoscope 31 can be utilized in both medical and industrial fields.

Figure 12:
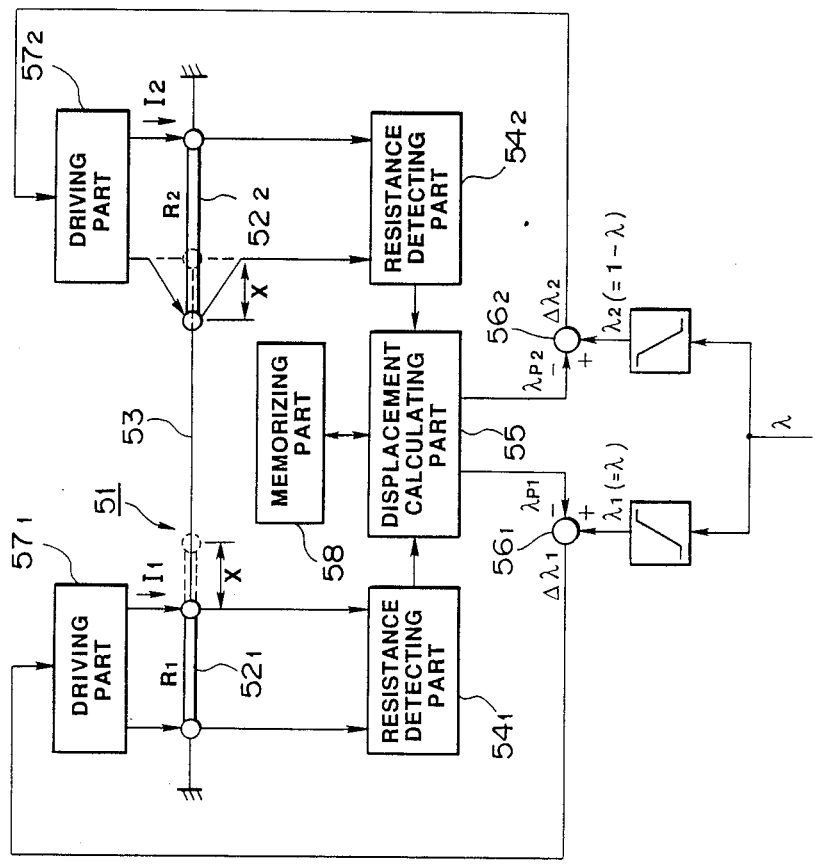
FIG. 12 is a formation diagram showing the sixth embodiment.

FIG. 12 shows the sixth embodiment of the present invention. An actuator 51 comprises shape memorizing alloy bodies $52_1$ and $52_2$, for example, of Ni-Ti and a connecting part 53 connecting them. In FIG. 12, the shape memorizing alloy body $52_1$ is shown to be in a high temperature state and the shape memorizing alloy body $52_2$ is shown to be in a low temperature state. The shape memorizing alloy bOdy $52_1$ at a lOW temperature and the shape memorizing alloy body $52_2$ at a high temperature are shown by the broken lines.

Resistance detecting parts (resistance detecting means) $54_1$ and $54_2$ are connected respectively to the shape memorizing alloy bodies $52_1$ and $52_2$, detect the resistance values $R_1$ and $R_2$ and output the resistance value signals.

A displacement calculating part (displacement calculating means) 55 receives resistance value signals output from the resistance detecting parts $54_1$ and $54_2$ calculates the displacement x of the actuator 51 on the basis of the respective resistance value signals and outputs the displacement signals $\lambda_{P1}$ and $\lambda_{P2}$.

Comparators (comparing means) $56_1$ and $56_2$ compare the displacement signals $\lambda_{P1}$ and $\lambda_{P2}$ output from the displacement calculating part 55 respectively with reference signals $\lambda_1$ and $\lambda_2$ to calculate their difference signals $\Delta\lambda_1$ and $\Delta\lambda_2$.

Driving parts (driving means) $57_1$ and $57_2$ receive the difference signals $\Delta\lambda_1$ and $\Delta\lambda_2$ output the comparators $56_1$ and $56_2$ and electrify and heat the shape memorizing alloy bodies $52_1$ and $52_2$ respectively with electric currents $I_1$ and $I_2$ proportional respectively to the difference signals $\Delta\lambda_1$ and $\Delta\lambda_2$ to drive the actuator 51.

When the actuator 51 is driven, the displacement signals $\lambda_{P1}$ and $\lambda_{P2}$ output from the displacement calculating part 55 will shift respectively to values close to the reference signals $\lambda_1$ and $\lambda_2$ and the difference signals $\Delta\lambda_1$ and $\Delta\lambda_2$ output respectively from the comparators $56_1$ and $56_2$ will become small. As a result, the displacement x of the actuator 1 will be held proportional to the values of the reference signals $\lambda_1$ and $\lambda_2$.

This normalized resistance value λ shows the rate of the mother phase occupied in the entire phase and there is a substantially linear relation between the normalized resistance value λ and the generated force or displacement. Therefore, by making the normalized resistance value λ an objective value, the displacement (position) of the actuator 51 can be controlled.

However, as described above, as the resistance value of the shape memorizing alloy body varies with the environment and fatigue, with conventional practice the maximum value R max and minimum value R min of the resistance value of the shape memorizing alloy body are determined in advance and these maximum value R max and minimum value R min are converted to the normalized resistance value which can not be said to correctly show the rate of the mother phase and has not been able to further precisely control the displacement (position).

Therefore, in this embodiment, just before driving the actuator 51, the maximum values R max and minimum values R min of the respective resistance values $R_1$ and $R_2$ of the shape memorizing alloys $52_1$ and $52_2$ are detected and can be stored in the memorizing part (memorizing means) 58.

For example, before being electrified and heated by the driving parts $57_1$ and $57_2$, the shape memorizing alloy bodies $52_1$ and $52_2$ are well cooled, the respective resistance values then of the shape memorizing alloy bodies $52_1$ and $52_2$ are detected by the resistance detecting parts $54_1$ and $54_2$ and the detected values are made the maximum values R max. Then, electric currents $I_1$ and $I_2$ sufficient to transform the shape memorizing alloy bodies $52_1$ and $52_2$ are fed from the driving parts $57_1$ and $57_2$ and, after the lapse of a time sufficient to end the transformation, the respective resistance values of the shape memorizing alloy bodies $52_1$ and $52_2$ are detected the same as is mentioned above and the detected values are made the minimum values R min. The thus determined maximum values R max and minimum values R min are stored in the memorizing part 58 through the displacement calculating part 55 so that, by determining the normalized resistance value $\lambda$ in the displacement calculating part 55 on the basis of these respective values, the correct mother phase rate may be shown and the displacement (position) of the actuator 1 may be precisely controlled.

It is apparent that, in the above mentioned embodiment, the shape memorizing alloy bodies $52_1$ and $52_2$ may be coil spring-like, linear or plate-like.

It is also apparent that the displacement calculating part 55 and memorizing part 58 may be formed, for example, of software by microcomputers.

The formations of the above mentioned resistance detecting parts $54_1$ and $54_2$ and driving parts $57_1$ and $57_2$ shall be explained in detail with reference to FIG. 15. Here shall be explained the shape memorizing alloy bodies $52_1$ and $52_2$ with the reference numeral 52, the resistance detecting parts $54_1$ and $54_2$ with $54_1$ the comparators $56_1$ and $56_2$ with 56 and the driving parts $57_1$ and $57_2$ with 57.

Figure 13:
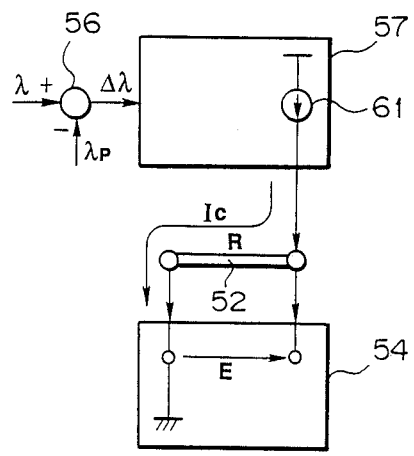

FIG. 13 shows examples of the resistance detecting part 54 and driving part 57. That is to say, the driving part 57 consists of a constant current circuit 61 feeding a constant current Ic to the shape memorizing alloy body 52. In the resistance detecting part 54, the voltage drop E by the resistance value R of the shape memorizing alloy body 52 is detected, is amplified with an amplifier (not illustrated) and is output as a resistance value signal. The above mentioned voltage drop E is proportional to the resistance value R as shown by the following formula:

$$E = Ic \cdot R$$

Figure 14:
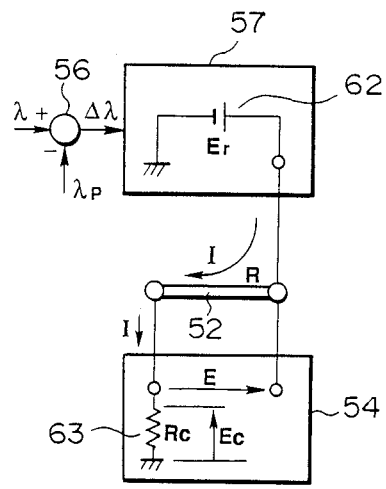

FIG. 14 shows other examples of the resistance detecting part 54 and driving part 57. That is to say, the driving part 57 is provided with a constant voltage circuit 62 to apply a constant voltage Er to the shape memorizing alloy body 52. On the other hand, the resistance detecting part 54 is provided with a resistor connected in series with the shape memorizing alloy body 52 and low in the resistance value so that, by determining respectively the voltage drop Ec by the resistance value Rc of the resistor 63 and the voltage drop E by the resistance value R of the shape memorizing alloy body 52, the resistance value R of the shape memorizing alloy body 52 may be determined from the following formula and a resistance value signal corresponding to the determined resistance value R may be output:

$$R = \frac{E}{Ec} \cdot Rc.$$

FIG. 15 shows other examples of the resistance detecting part 54 and driving part 57 wherein PWM (pulse width modulated) electrifying heating is used. The shape memorizing alloy body 52 is driven by a driving pulse A (See FIG. 16) output from a switching circuit 64 of the driving part 57 so as to be transformed. The shape memorizing alloy body 52 is connected to a resistance bridge circuit 65 of the resistance detecting part 54 and a signal corresponding to the resistance value of the shape memorizing alloy body 52 is output from this bridge circuit 65. The output signal of the bridge circuit 65 is amplified by an amplifier 66 and is then fed to a sampling-holding circuit (S/H) 67 which sample-holds the output signal of the amplifier 66 by a sampling pulse B output during the off-period of the driving pulse A from a later described PWM circuit 69. The sample-held signal is input into the displacement calculating part 55. A difference signal $\Delta\lambda$ is calculated in the comparator 56 and is fed back to a controller 68 of the driving part 57. The signal from the controller 68 is input into the PWM circuit 69. By controlling the switching circuit 64 with this PWM circuit 69, the pulse width of the driving pulse A is variably controlled in the direction of making the difference signal $\Delta\lambda$ small and the shape memorizing alloy body 52 is driven by the switching circuit 64.

In the above mentioned embodiment, the applied voltage of the driving pulse A is made constant but may be kept variable in response to the kind of the shape memorizing alloy body 52 or the load.

The driving part 57 is shown to be only of electrifying heating but may be of induction heating or heating by a chemical reaction.

Figure 17:
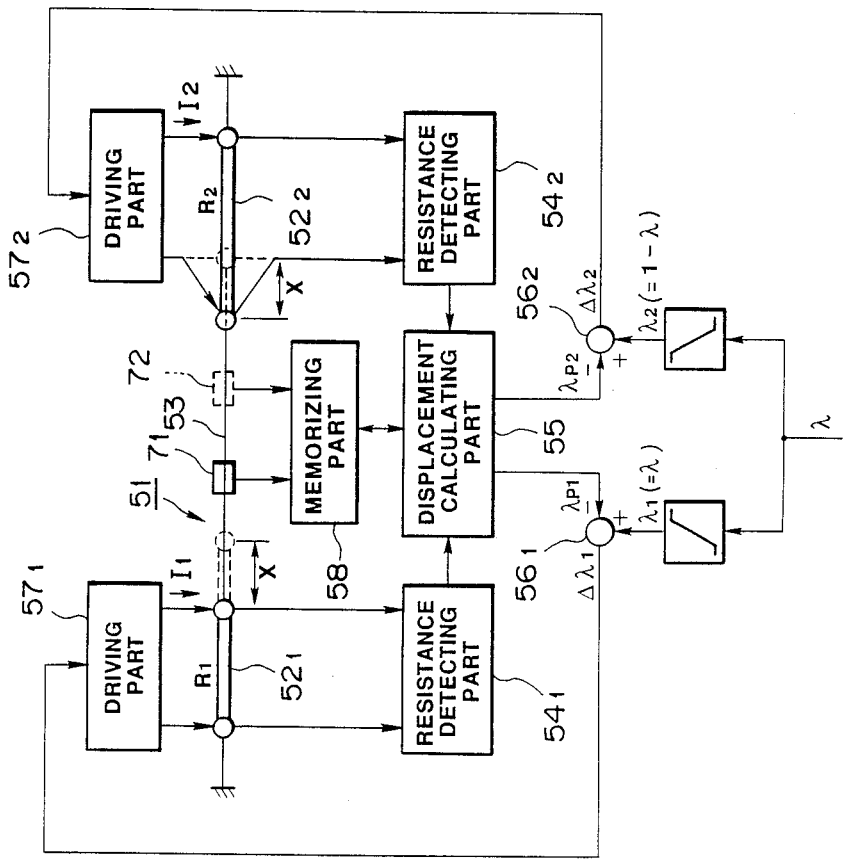
FIG. 17 is a formation diagram showing the seventh embodiment.

FIG. 17 shows the seventh embodiment of the present invention. This embodiment is of substantially the same formation as of the sixth embodiment except the actuator 1 being provided with a position sensor or force sensor 72. These sensors 71 and 72 are to be used just before driving the actuator 51 to determine the maximum value R max and minimum value R min of the respective resistance values $R_1$ and $R_2$ and can be used even for the use which can not be fitted at the time of the actual use.

The respective information the above mentioned sensors 71 and 72 are to stored in the memorizing part 58 the information of the position and/or force simultaneously in response to the resistance values at fixed intervals within the resistance value varying width in the case of detecting the maximum value R max and minimum value R min of the respective resistance values $R_1$ and $R_2$ of the shape memorizing alloy bodies $52_1$ and $52_2$ Thus, in the sixth embodiment, only the fluctuation of the resistance values of the shape memorizing alloy bodies $52_1$ and $52_2$ is compensated but, in this seventh embodiment, the position or force of the actuator 51 can be simultaneously compensated and therefore a further precise position control is possible.

In the above mentioned sixth and seventh embodiments, by using a so-called PID controller for the controller within the driving part 57, from the response when determining the maximum value and minimum value of the resistance value of the shape memorizing alloy body, parameters (a proportion gain, integrating time and differentiating time) may be automatically tuned.

Figure 18:
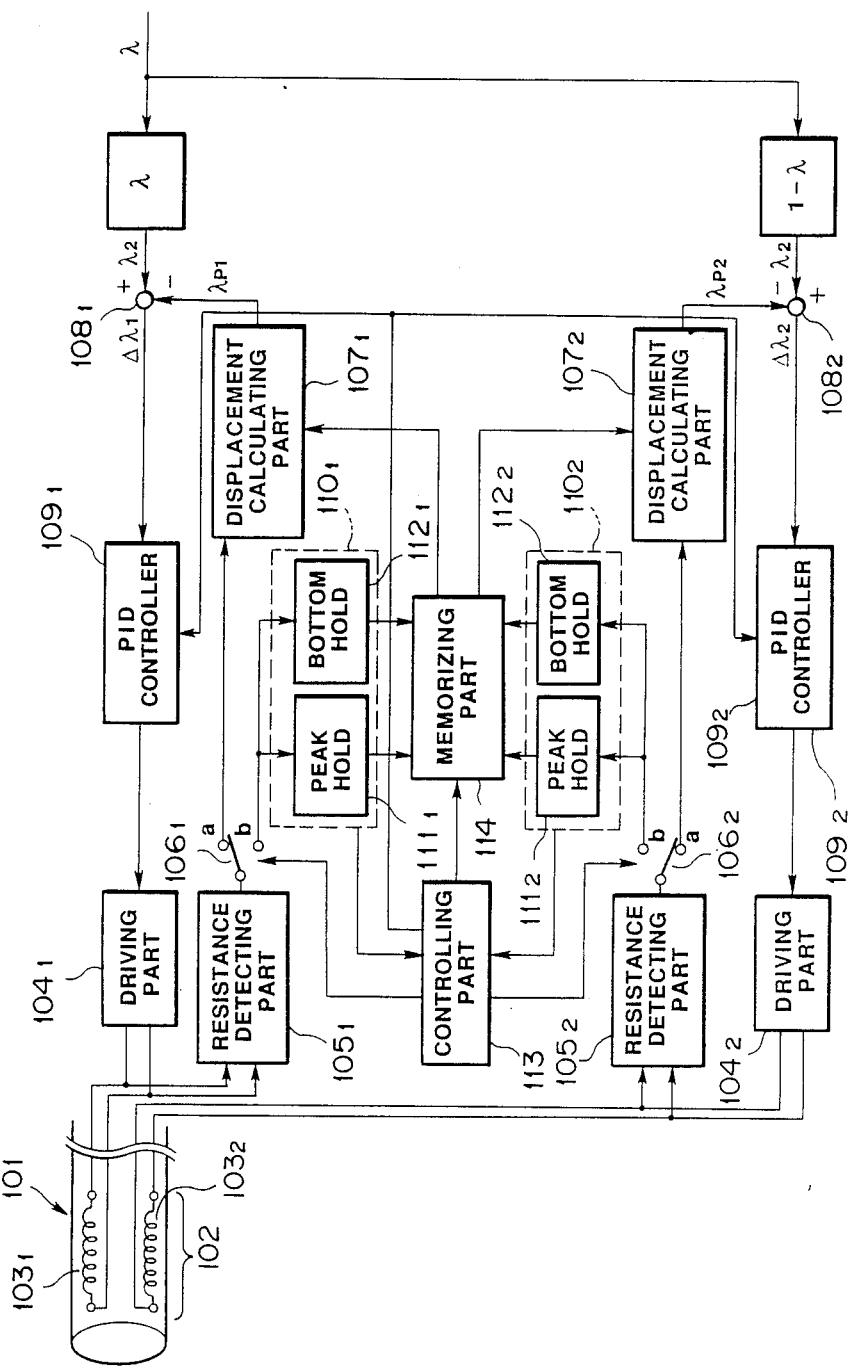
FIG. 18 is a formation diagram showing the eighth embodiment.

FIG. 18 shows the eighth embodiment of the present invention. This embodiment further defines the fifth embodiment shown in FIG. 9. Within a curvable part 102 at the tip of an endoscope 101, a pair of coil spring-like shape memorizing alloy bodies $103_1$ and $103_2$ are arranged respectively as deviated by 180 degrees with respect to the center axis. The shape memorizing alloy bodies $103_1$ and $103_2$ are connected respectively to driving circuits $104/_1$ and $104_2$ so as to be electrified and heated by these driving circuits $104_1$ and $104_2$ and to be curved by shrinking in the axial direction of the endoscope 101.

When the shape memorizing alloy bodies $103_1$ and $103_2$ are electrified and heated as mentioned above, their resistance values will vary and will be detected by resistance detecting parts $105_1$ and $105_2$ connected respectively to the shape memorizing alloy bodies $105_1$ and $105_2$. The detected resistance values, that is, the resistance value signals output from the resistance detecting parts $105_1$ and $105_2$ are fed to displacement calculating parts $107_1$ and $107_2$ respectively through the sides a of switching switches $106_1$ and $106_2$, are converted here respectively to displacement signals $\lambda_{P1}$ and $\lambda_2$.

Into the comparators $108_1$ and $108_2$ are input respectively operating signals $\lambda_1$ and $\lambda_2$ in response to the operating input $\lambda$. The comparators $108_1$ and $108_2$ compare respectively the operating signals $\lambda_1$ and $\lambda_2$ with the displacement signals $\lambda_{P1}$ and $\lambda_{P2}$ and output their difference signals $\Delta\lambda_1$ and $\Delta\lambda_2$ to PID controllers $109_1$ and $109_2$ which transmit control signals respectively to the driving circuits $104_1$ and $104_2$ to electrify the shape memorizing alloy bodies $103_1$ and $103_2$ in response to the above mentioned difference signals $\Delta\lambda_1$ and $\Delta\lambda_2$.

When the displacement of the curvable part 102 is thus controlled, the switching switches $106_1$ and $106_2$ will be connected to the side a.

The resistance value signals output from the resistance detecting parts $105_1$ and $105_2$ are transmitted respectively to peak holding circuits $111_1$ and $111_2$ and bottom holding circuits $112_1$ and $112_2$ within resistance variation width detecting parts $110_1$ and $110_2$ through the side b of the switching switches $106_1$ and $106_2$.

Just before using the endoscope 101, a controlling part 113 sets the switching switches $106_1$ and $106_2$ respectively on the sides b, transmits respectively to PID controllers $109_1$ and $109_2$ control signals as gradually heat the shape memorizing alloy bodies $103_1$ and $103_2$ and electrifies and heats the shape memorizing alloy bodies $103_1$ and $103_2$ until they are well curved (to a point Af at which the resistance value is minimum). At this time, by the peak holding circuits $111_1$ and $111_2$ and bottom holding circuits $112_1$ and $112_2$ of the resistance variation width detecting parts $110_1$ and $110_2$, the maximum values and minimum values of the resistance values of the shape memorizing alloy bodies $103_1$ and $103_2$ are detected and can be stored in the memorizing part 114.

The operation in FIG. 18 shall be explained in the following. First of all, the operating signal $\lambda$ ($0 \leq \lambda \leq 1$) input from an operating part (not illustrated input as operating signals $\lambda_1$ and $\lambda_2$ in response to the curving direction and curvature of the shape memorizing alloy bodies $103_1$ and $103_2$. At this time, as operating signals, $\lambda_1 = \lambda$ is input into one shape memorizing alloy body $103_1$ and $\lambda_2 = 1 - \lambda$ is input into the other shape memorizing alloy body $103_2$. As the same operation is made on the respective shape memorizing alloy bodies $103_1$ and $103_2$, one shape memorizing alloy body $103_1$ shall be explained hereinafter.

The operating signal $\lambda_1$ is input into the PID controller $109_1$ and a control signal is output so that a curvature corresponding to the operating signal $\lambda_1$ may be obtained and may be quickly reached and is input into the driving circuit $104_1$. At this time, the operating signal $\lambda_1$ represents a normalized resistance. As this normalized resistance is defined by the resistance value variation width of the shape memorizing alloy body $103_1$, it is necessary to obtain a correct resistance value variation width.

Figure 19:
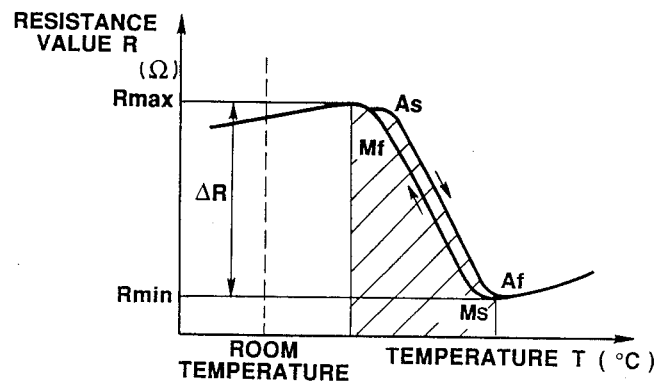
FIG. 19 is a diagram showing the relationship between the temperature and resistance value of the shape memorizing alloy body for explaining the operation of FIG. 18.

Therefore, in the controlling part 113, just before using the endoscope 101, in order to measure the resistance value variation width $\Delta R$ of the shape memorizing alloy body $103_1$, a control signal is transmitted to the PID controller $109_1$ which operates the driving circuit $104_1$ so that the shape memorizing alloy body $103_1$ may be electrified and heated sufficiently to be at the point Af from the point As in FIG. 19.

At this time, the electrified and heated shape memorizing alloy body $103_1$ slightly increases in the resistance value in the range from the room temperature to the point As. After the maximum value is shown at the point As, the resistance value begins to quickly decrease and shows the minimum value at the point Af. After the point Af, the resistance value begins to increase again though slightly.

In order to determine the maximum resistance value and minimum resistance value, the controlling part 113 has the switching switch $106_1$ set on the side b to connect the resistance detecting part $105_1$ and resistance variation width detecting part $110_1$ with each other. In the peak holding circuit $111_1$ and bottom holding circuit $112_1$ within the resistance variation width detecting part $110_1$, the maximum resistance value R max and minimum resistance value R min are respectively detected and are stored in a memorizing part 114.

After the end of the detection of the maximum resistance value R max and minimum resistance value R min, the controlling part 113 has the switching switch $106_1$ switched to be set on the side a and further outputs to the displacement calculating part $107_1$ the maximum resistance value R max and minimum resistance value R min memorized in the memorizing part. When the endoscope 101 is actually operated, the resistance value of the shape memorizing alloy body $103_1$ will be detected by the resistance detecting part $105_1$ and will be input into the displacement calculating part $107_1$.

The displacement calculating part $107_1$ normalizes the resistance value signal input from the resistance detecting part $105_1$ with the maximum resistance value R max and minimum resistance value R min input in advance and feeds it as a normalized resistance signal $\lambda_{P1}$ to the comparator $108_1$. In the comparator $108_1$, the difference between the operating signal $\lambda_1$ and normalized resistance signal $\lambda_{P1}$ is taken and the difference signal $\Delta\lambda_1$ is input into the PID controller $109_1$ to obtain any desired curvature.

The formations of the above mentioned resistance variation width detecting parts $110_1$ and $110_2$ shall be explained in detail in the following with reference to FIGS. 20 to 21. Here shall be explained the shape memorizing alloy bodies $103_1$ and $103_2$ with the reference numeral $103_1$ the resistance detecting parts $105_1$ and $105_2$ with 105, the switching switches $106_1$ and $106_2$ with 106, the PID controllers $109_1$ and $109_2$ with 109, the resistance variation width detecting parts $110_1$ and $110_2$ with 110, the peak holding circuits $111_1$ and $111_2$ with 111 and the bottom holding circuits $112_1$ and $112_2$ with 112.

FIG. 22 shows an example of the resistance variation width detecting part 110. The controlling part 113 has the PID controller make the electrification and heating large enough to determine the maximum resistance value R max and minimum resistance value R min which are determined by the peak holding circuit 111 and bottom holding circuit 112 and is then required to quickly stop the electrification and heating of the shape memorizing alloy body 103. If the shape memorizing alloy body 103 is further continued to be electrified and heated after the point Af, the shape memorizing alloy body 103 will be likely to forget the memorized shape and the fatigue characteristics will deteriorate to make the lifespan short.

Therefore, the output of the bottom holding circuit 112 and the output of the resistance detecting part 105 are amplified by an operating amplifier 121 and its output is input into a comparator 122 in which a threshold voltage VS is set in advance so that, when the resistance value becomes larger by any value than the minimum resistance value R min of the shape memorizing alloy body 103 (in case the shape memorizing alloy body 103 is further heated to be of a larger resistance value), the comparator 122 may output its output to the controlling part 113 which may output a control signal to the PID controller 109 to stop the electrification and heating.

Figure 20:
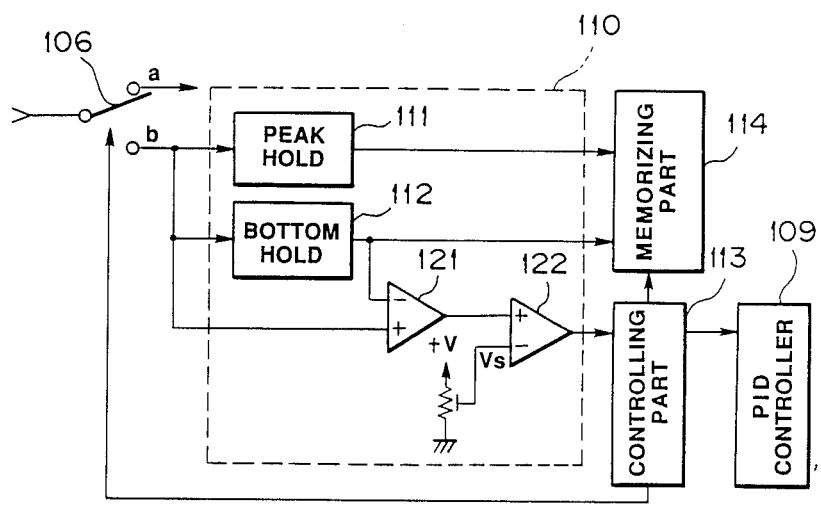

According to the above explained resistance variation width detecting part 110 in FIG. 20, the resistance value variation width can be correctly detected and the curvature can be precisely controlled. Since the electrification and heating of the shape memorizing alloy body 103 are stopped after the minimum resistance value is detected, the time for detecting the resistance value variation width can be remarkably shortened.

FIG. 21 shows another example of the resistance variation width detecting part 110. The respective inputs of a sample holding circuit 123 and first differentiator 124 are connected to the side b of the switching switch 106. The output of the first differentiator 124 is connected to the input of a second differentiator 125. The output of the second differentiator 125 is fed to the controlling part 113 through a comparator 126. The controlling part 113 feeds the sample holding circuit 123 and a memorizing part 114 with trigger signals on the basis of the output of the comparator 126. The output of the sample holding circuit 123 is stored in the memorizing part 114.

In such a formation, the operation in FIG. 21 shall be explained with reference to FIG. 22. FIG. 22(a) shows an output voltage waveform of the resistance detecting part 105 to obtain an output proportional to the resistance value variation of the shape memorizing alloy body 103. If the shape memorizing alloy body 103 is electrified and heated over the time, first the output voltage will rise though slightly but, when the point As is reached, the output voltage will begin to quickly reduce and will begin at the point Af to rise again though slightly.

When this output voltage is input into the first differentiator 124, the output voltage will be a differential waveform as in FIG. 22(b). When the output voltage of the first differentiator 124 is further input into the second differentiator 125, the output voltage will be a differential waveform as in FIG. 22(c). The pulse waveform of this output voltage shows inflection points of the waveform in FIG. 22(a). These inflection points represent the maximum resistance value and minimum resistance value. Therefore, when the output voltage of the second differentiator 125 is input into the controlling part 113 through the comparator 126, in the controlling part 113, on the basis of this, trigger signals are fed to the sample holding circuit 123 and memorizing part 114 to store the maximum resistance value and minimum resistance value in the memorizing part.

In the controlling part 113, after the positive pulse waveform of the output voltage of the second differentiator 125 is detected, t stop the electrification and heating of the shape memorizing alloy body 103, a control signal is fed to the PID controller 109 and th switching switch 106 is switched to be set on the side a.

By the above operation, the maximum resistance value R max and minimum resistance value R min of the shape memorizing alloy body 103 can be correctly measured.

In the above mentioned explanation, the maximum resistance value R max and minimum resistance value R min of the shape memorizing alloy body 103 are detected and the normalized resistance $\lambda$ is determined. However, in case precision is required or in case a large displacement is required, the normalized resistance $\lambda$ will be able to be varied in response to it. For example, in case a high precision is required, only the range in which the linearity is high (near the middle between the points As and Af) may be used. For example, if 10% at both ends of $\Delta\lambda$ is removed, $$R\ max' = R\ max - 0.1\ \Delta R$$
$$R\ min' = R\ min + 0.1\ \Delta R$$
$$\therefore \lambda = \frac{R\ max - R - 0.1\ \Delta R}{R\ max - R\ min - 0.2\ \Delta R}.$$

It is also apparent that, in case a large displacement is required, the entire range of the determined maximum resistance values R max and minimum resistance values R min may be used.

Figure 23:
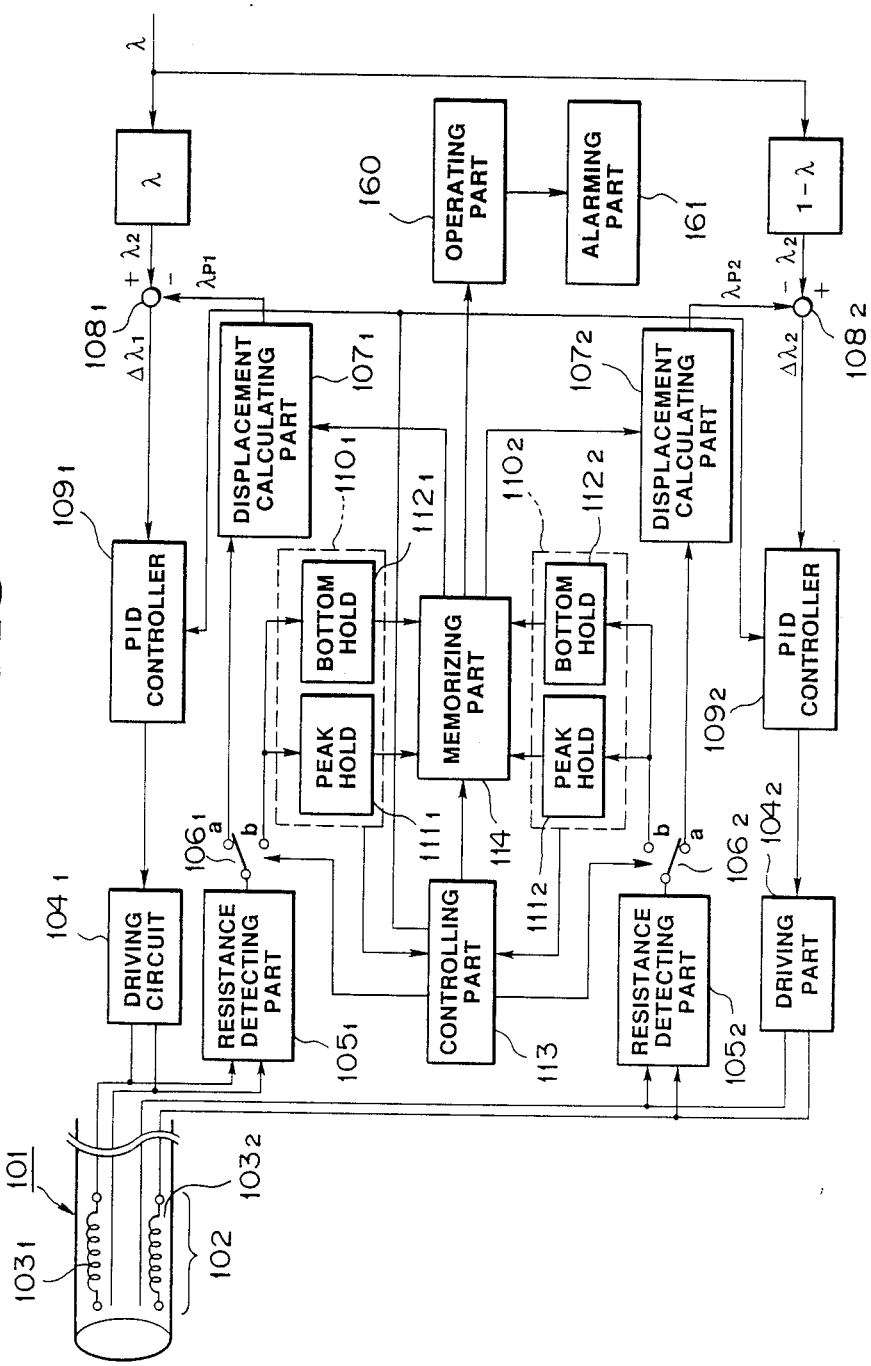
FIG. 23 is a formation diagram showing the ninth embodiment.
Figure 24:
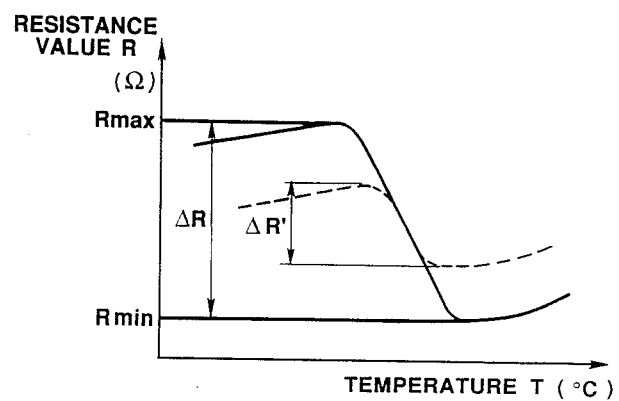
FIG. 24 is a diagram showing the relationship between the temperature and resistance value of the shape memorizing alloy body for explaining the operation of FIG. 23.
Figure 32:
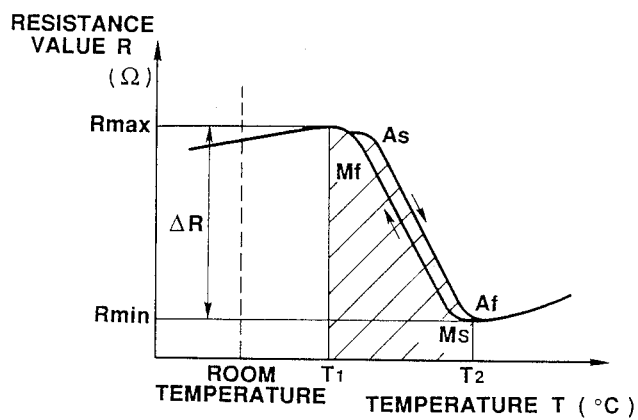
FIGS. 31 and 32 relate to the 11th embodiment.

FIG. 23 shows the ninth embodiment of the present invention.

In this embodiment, an operating part 160 is connected to the memorizing part 114 of the eighth embodiment and an alarming part 161 provided with a buzzer or LED is connected to this operating part 160.

Figure 25:
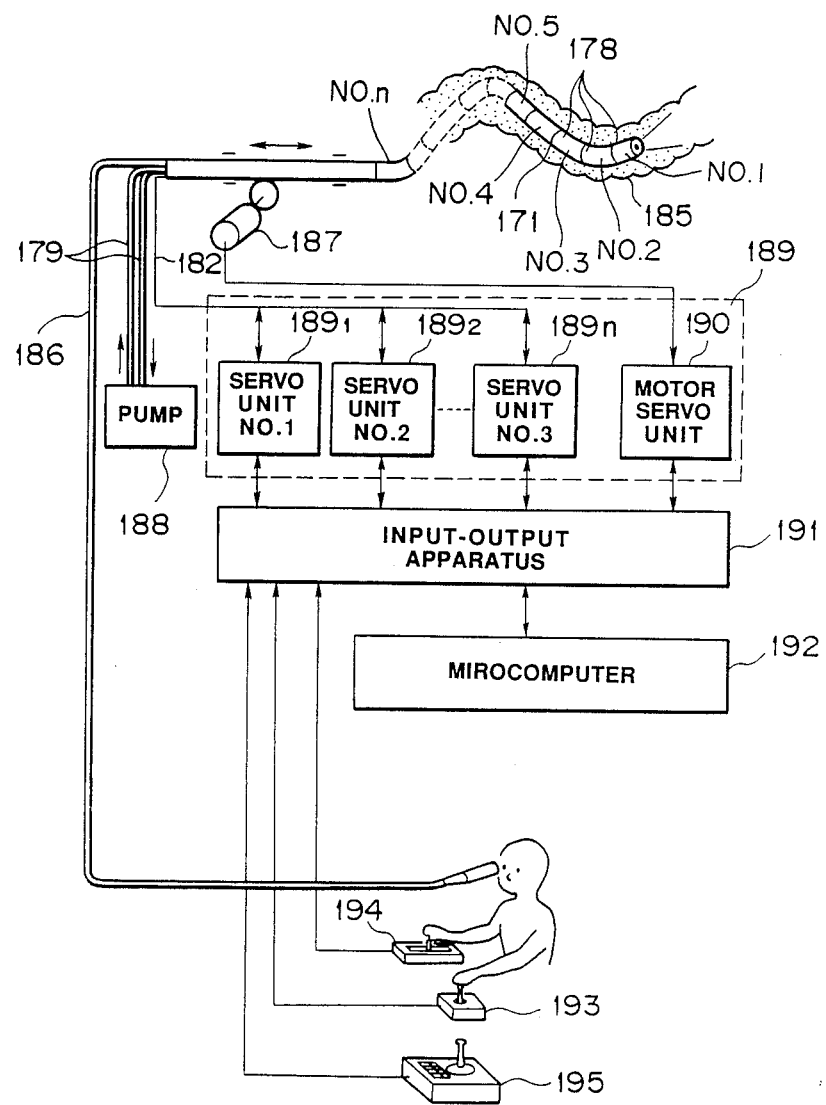
FIG. 25 is a formation view showing the tenth embodiment.

When the shape memorizing alloy body 103 is used for a long time, its characteristics will deteriorate, no sufficient displacement will be obtained and the resistance value variation width will vary from $\Delta R$ to $\Delta R'$ as shown in FIG. 25. In such a case, the operating part 160 will control the alarming part 161 to sound the alarm or light the LED.

The above mentioned operating part 160 inputs the maximum resistance value R max and minimum resistance value R min stored in the memorizing part 114 and operates ΔR=R max−R min. In case this ΔR is compared with preset ΔRT and ΔR<ΔRT, the operating part 160 will output a control signal to the alarming part 111. When the alarming part 161 receives the control signal, it will sound the alarm with the buzzer or will light the LED to inform the operator that the ΔR has become smaller than the preset ΔRT.

In this embodiment, the variation of the displacement of the shape memorizing alloy body 103 caused by long time use can be easily known.

Figure 26:
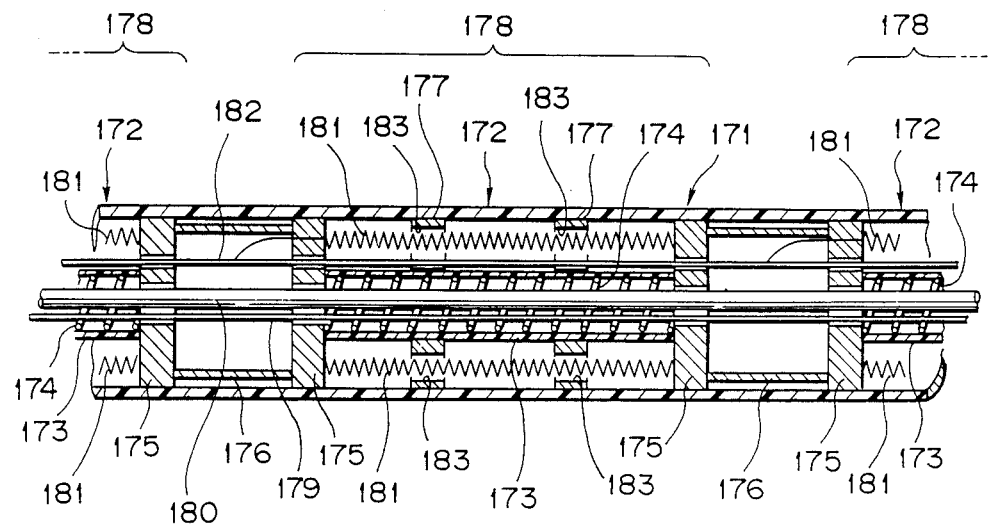
FIG. 26 is a sectioned view of an endoscope shown in FIG. 25.
Figure 27:
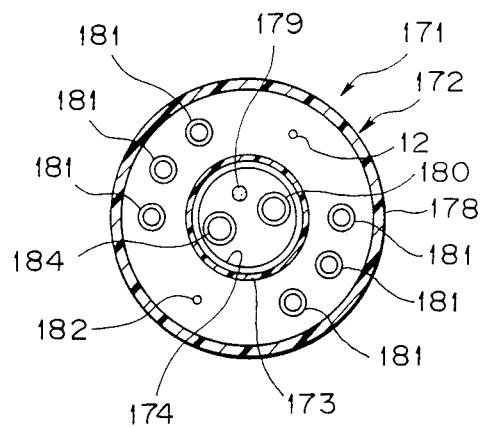
FIG. 27 is a radially sectioned view of FIG. 26.

FIG. 25 shows the tenth embodiment of the present invention. FIG. 26 is a sectioned view in the axial direction of an insertable part 171 of an endoscope. FIG. 27 is a sectioned view in the radial direction of the insertable part 171. The insertable part 171 is covered on the outer periphery with an outer coating 172 and is provided in the center with a tube 173 through which a coil spring 174 is arranged in the axial direction to keep the shape of the insertable part 171 linear.

The insertable part 171 consists of a plurality of articulate bodies 178. Each articulate body is provided at both ends with flanges 175. The flanges 175 of the adjacent articulate bodies 178 are connected with each other through a pillar 176. Two intermediate flanges 177 are provided within each articulate body 178. The intermediate flange 177 is provided with inserting holes 183 through which shape memorizing alloy coils (abbreviated as SMA coils hereinafter) 181 are to be respectively inserted.

An air feeding pipe line 179 for generating an air stream to cool the later described SMA coils 181 and component parts of the endoscope such as an image guide fiber 180 and a light guide fiber (not illustrated) are arranged within the tube 173.

Each articulate body 178 has six SMA coils 181 fixed at both ends to the flanges 175. The SMA coil 181 has been made to store the shape of a closely wound state at a temperature above the transformation point and is fixed as stretched and transformed at a temperature below the transformation point. Therefore, when it is heated to a temperature above the transformation point, it will shrink. The material of the SMA is properly selected from among such various materials as a Ti-Ni alloy and Cu-Zn-Al alloy.

As shown in FIG. 27, three SMA coils are provided on each of both sides holding the tube 173. Therefore, when three SMA coils 181 on one side are selectively heated to a temperature above the transformation point, the articulate 178 will be able to be bent in that direction. As the heating is made by Joule heat by electrification the three SMA coils 181 on one side of the tube 173 will be properly connected at the ends with one another, will be electrically connected in series and will be electrified in series. The three series connected SMA coils 181 are connected at one end to a common lead wire for grounding in a lead wire bundle 182 and are connected at the other end to the respective lead wires in the lead wire bundle 182.

FIG. 25 shows a block diagram of an endoscope system having an insertable part 171 consisting of n articulate bodies 178 formed as described above. The insertable part 171 is inserted into the large intestine 185 and the intestine wall is observed with a fiber scope 186 from the tip.

Outside a human body are provided a servo-motor to insert the insertable part 171 into the large intestine by moving, a controlling apparatus 189 controlling to insert and bend the insertable part 171 and a pump 188 feeding cooling air into the insertable part 171 through the air feeding pipe line 179.

The controlling apparatus 189 comprises servo units $189_1$, $189_2$, and $189_n$ as commanding parts controlling the bending angles of the respective articulate bodies 178, a motor servo unit 190 controlling the moving speed and the controlling part 8 described in the first embodiment. The servo units $189_1$, $189_2$, ... and $189_n$ are connected with the SMA coils 181 of the corresponding articulate bodies 178 through the lead wire bundle 182, electrify the SMA coils 181 on the basis of the command from a microcomputer 192 given through an input-output apparatus 191 and heat them with Joule heat. An electric resistance value representing the actual bending angle of the SMA coil 181 is fed back to the servo units $189_1$ to $189_n$.

Figure 28:
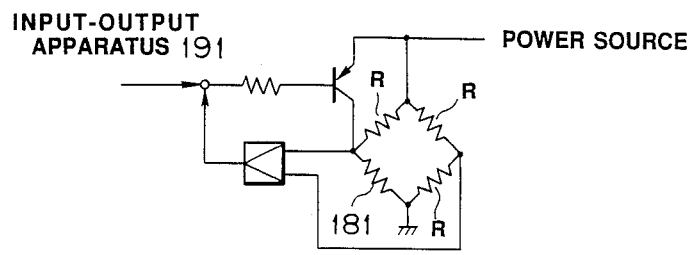
FIG. 28 is a formation diagram of a servo unit shown in FIG. 25.

As shown in FIG. 28, each of the respective servo units $189_1$ to $189_n$ incorporates the SMA coil 181 and three resistances R of a fixed resistance value into a bridge circuit, feeds back the electric resistance value of the SMA coil 181 and applies it to a bending angle signal fed through the input-output apparatus 191. FIG. 28 shows an electrifying circuit for the SMA coil 181 on one side. In fact, each servo unit 189 is provided with two such electrifying circuits. Therefore, until the angle of the bending command and the electric resistance value of the SMA coil 181 coincide with each other, the SMA coil 181 on the side in the direction responding to the bending command is electrified and the articulate body 178 bends by the angle responding to the bending command in the direction responding to the bending command.

Returning to the explanation of FIG. 25, to the input-output apparatus 191 are connected also a tip controlling lever 193 setting the objective value of the bending angle of the articulate body 178 at the tip (No. 1), an inserting operation lever 194 and an auxiliary handling part 195.

Each of the tip controlling lever 193 and inserting operation lever 194 generates a commanding signal showing the bending angle (including the direction) and inserting speed responding to the lever operating amount.

Figure 29:
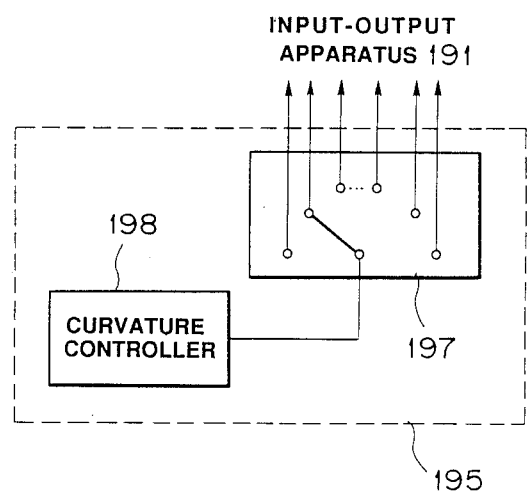
FIG. 29 is a formation diagram of an auxiliary handling part shown in FIG. 25.

As shown in FIG. 29, the same as the tip controlling lever 193, the auxiliary handling part 195 comprises a curvature controller 198 setting the objective value of the bending angle of an articulate body objective value of the bending angle of an articulate body and a switching switch 197 for selectively setting the command signal from the curvature controller 198 into any one of the servo units $189_1$ to $189_n$ through the input-output apparatus 191. The output of the switching switch 197 is fed to the micro-computer 192 through the input-output apparatus 191 and the command signal fed to the corresponding servo units $189_1$ to $189_n$ is corrected.

The resistance value R of the SMA coil 181 is compared with the maximum resistance value R max and minimum resistance value R min by the controlling part 8. The controlling part 8 will have the servo units $189_1$ to $189_n$ stop the cooling of the SMA coil 181 in case R>R max and stop the electrification of the SMA coil 181 in case R<R min.

Figure 30:
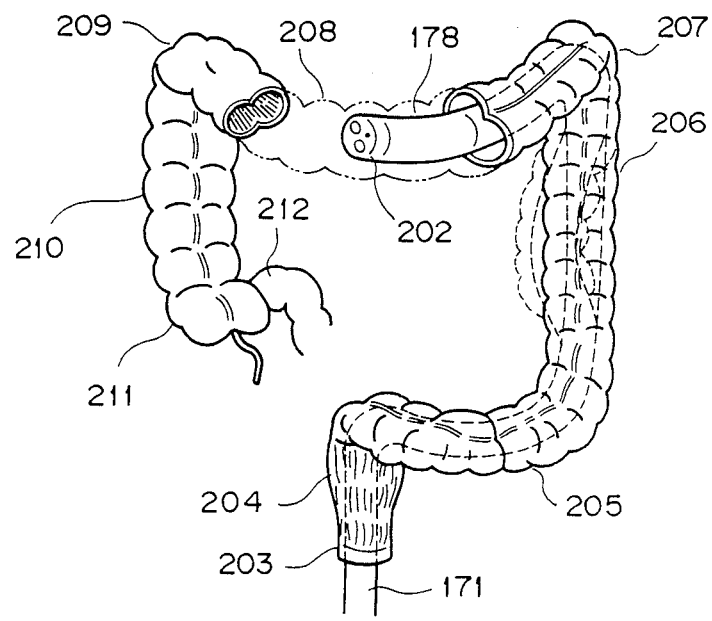
FIG. 30 is an explanatory view of the use of the endoscope shown in FIG. 25.

FIG. 30 shows the manner of inserting the endoscope of this embodiment into the large intestine. The tip part 202 of the insertable part 171 is inserted to the lateral colon 208, right colon bend 209 and ascending colon 210 through the anus tube 203 of the large intestine, rectum 204, S-colon 205, descending colon 206 and left colon bend 207. The reference numeral 211 represents the appendix and 212 represents the ileum.

The operation of this embodiment shall be explained in the following.

While seeing the image of the inner wall of the large intestine with the fiber scope 186, the tip controlling lever 193 and insertion operating lever 194 are handled. A command given manually from these levers is input into the microcomputer 192 through the input-output apparatus 191, is processed by the microcomputer 192 and is then fed to the respective servo units $189_1$ and 190 again through the input and output apparatus 191.

Here, the command from the lever 193 is given to the servo unit $189_1$ and the SMA coil 181 of the articulate body 8 at the tip is electrified and heated by the servo unit $189_1$.

The SMA coil 181 has a property of being comparatively soft and elongatable at a temperature below the transformation point of about 70° C. but will become hard and will return to the memorized shape when heated to be above the transformation point. That is to say, when the SMA coil 181 is not electrified, the articulate body 178 will linearly stretch due to the resiliency of the coil spring 174 but, when the SMA coil 181 on either side is electrified, due to the Joule heat, the SMA coil 181 will reach a temperature above the transformation point and will shrink. As a result, the articulate body 178 will bend on the side of the electrified SMA coil 181. Thus, determining which SMA coil 181 is to be electrified is the bending direction command and determining the electrification amount is the bending angle command. The SMA coil 181 will vary in the electric resistance value with this phase transformation. However, as shown in FIG. 28, when the electrifying current is controlled by feeding back the resistance value, the bending angle will coincide with the commanded angle.

The command from the lever 194 is given to the servo-motor unit 190, the servo-motor 187 is driven on the basis of the command signal and the insertable part 1 is inserted at the commanded speed.

In the initial period, no command is given to the servo units $189_2$ to $189_n$ and the other articulate bodies 178 than at the tip remain straight.

When the insertable part 171 is inserted by the distance of one pitch of the articulate body 178 by the rotation of the servo-motor 187, a shifting command will be issued from the microcomuter 192 and the command which has been given to the respective servo units $189_1$ to $189_{n-1}$ will be shifted to the subsequent servo units $189_2$ to $189_n$. That is to say, the SMA coil of the articulate body second from the tip is being electrified with the electrifying amount so far given to the SMA coil of the articulate body at the tip. The bend of the articulate body at the tip is always based on the command input from the tip controlling lever 193.

Thereby, if the bending command for the articulate body at the tip is input from the lever 193, the subsequent articulate bodies will bend in the same manner in turn as synchronized with the insertion of the insertable part 171. Therefore, the insertable part 171 is inserted while being bent along the bent shape of the large intestine 185.

When the electrification of the SMA coil 181 is stopped, the SMA coil 181 will be cooled to a temperature below the transformation point by air circulating through the air feeding pipe line 179 and will lose the shrinking force and therefore the articulate body 178 will be returned to be linear by the resiliency of the coil spring 174.

As explained above, according to this embodiment, by only giving the bending command to the tip articulate body, the subsequent articulate bodies will be bent in the same manner in turn as synchronized with the insertion of the insertable part.

Figure 31:
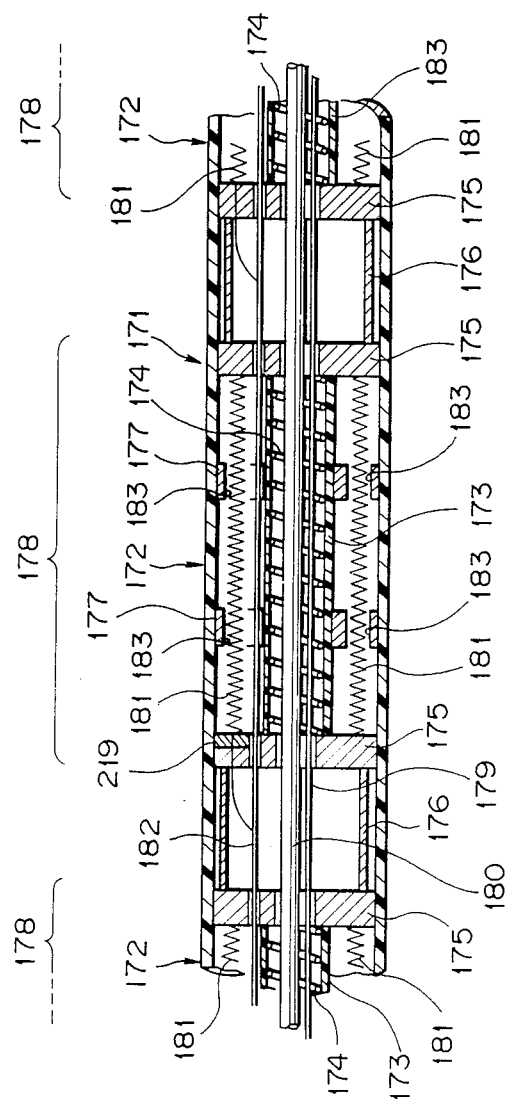

FIG. 31 shows the 11th embodiment of the present invention.

In this embodiment, the insertable part 171 of the endoscope of the tenth embodiment is provided with a temperature sensor 219 detecting the temperature of the SMA coil 181.

The above mentioned temperature sensor 219 is provided in contact with the SMA coil 181 in the flange 175 so that the temperature T of the SMA coil 181 in case it is heated or cooled may be measured. In case a preset temperature $T_1$ (the temperature when the resistance value R of the SMA coil 181 is equal to the maximum value R max) and a temperature $T_2$ (when it is equal to the minimum value R min) are reached, the resistance values R of the SMA coil 181 will be measured and will be made respectively the maximum value R max and minimum value R min.

According to this embodiment, as the temperature is measured, in the process of measuring the maximum value R max and minimum value R min, overheating and overcooling can be prevented.

For the above mentioned temperature sensor 219, a thermocouple (of a T type) is fixed to the SMA coil 181 by spot-welding so that the temperature of the SMA coil 181 itself may be correctly measured. The temperature sensor 219 is not limited to be a thermocouple but a temperature sensor such as a thermistor may be provided within the flange 175 to be fixed in close contact with the SMA coil 181.

The other formations, operations and effects are the same as in the tenth embodiment.

FIGS. 33 to 37 show the 12th embodiment of the present invention.

In these drawings, the reference numeral 221 represents an endoscope and 222 represents a light source apparatus.

The above mentioned endoscope 221 has an elongate flexible insertable part 223 insertable into a body cavity and a thick operating part 224 connected this insertable part 223 on the base end side and having a universal cord 225 extended from one side. The universal cord 225 is provided at the tip with a connector apparatus 225a connected to the connector receptacle of the above mentioned light source apparatus 222 so that the above mentioned universal cord 225 may be connected to the above mentioned light source apparatus 222 through this connector apparatus 225a. An illuminating light by the light source apparatus 222 is led to the tip part 226 through a light guide arranged within the above mentioned insertable part 223 so as to be radiated to a part to be observed.

A curvable part 227 is provided on the base end side of the above mentioned tip part 226 and has a driving member 228 made of a thermosensitive transformable member formed, for example, to be belt-like built-in in the axial direction. This driving member 228 is formed of a shape memorizing alloy as, for example, a Ti-Ni alloy or Cu-Zn-Al alloy so that, when heated to be above the transformation point, it may be transformed to be of the shape memorized in advance and the above mentioned curvable part 227 may be curved.

A pair of electric wires 229 are connected at one end to this driving member 228 and are extended at the other end into the universal cord 225 through the above mentioned operating part 224 so as to be connected through the connector apparatus 225a to a resistance value detecting part 231 provided within the above mentioned light source apparatus 228.

This resistance value detecting part 231 is connected also to a resistance value linearly varying part detecting circuit 232 and logarithm-index converting part 242 which is an example of a converting means so that the resistance value of the above mentioned driving member 228 may be detected by the resistance value detecting part 231 and this detected result may be output to these resistance value linearly varying part detecting circuit 232 and logarithm-index converting part 242. A resistance value sensing means 230 is formed of the above mentioned resistance value detecting part 231 and resistance value linearly varying part detecting circuit 232.

Further, the resistance value detecting part 231 is connected to the controlling part 8 described in the first embodiment so that the resistance value of the driving member 228 may be compared with the maximum resistance value R max or minimum resistance value R min and an electrification controlling circuit 246 may be commanded to stop the cooling in case R>R max or to stop the electrification in case R<R min.

Figure 34:
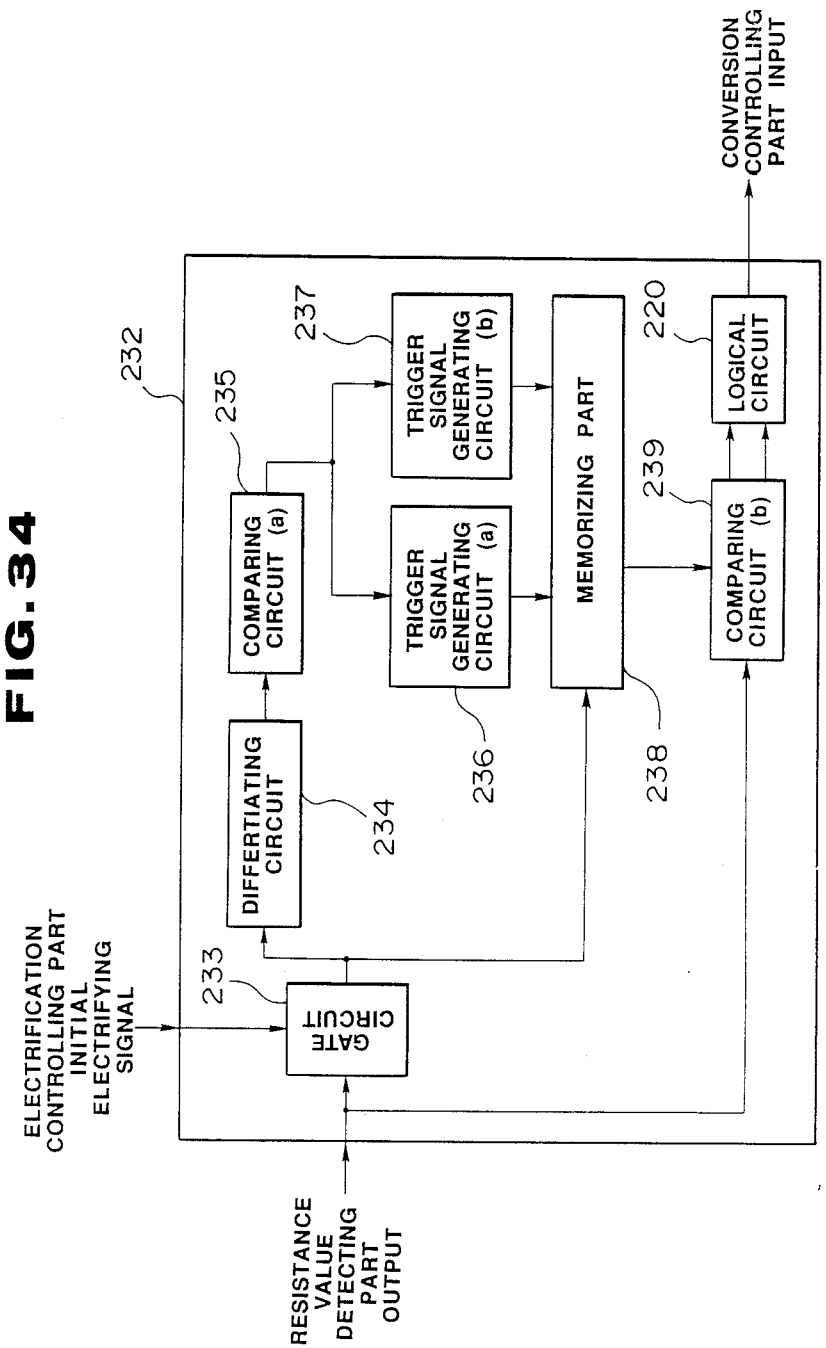
Figure 37:
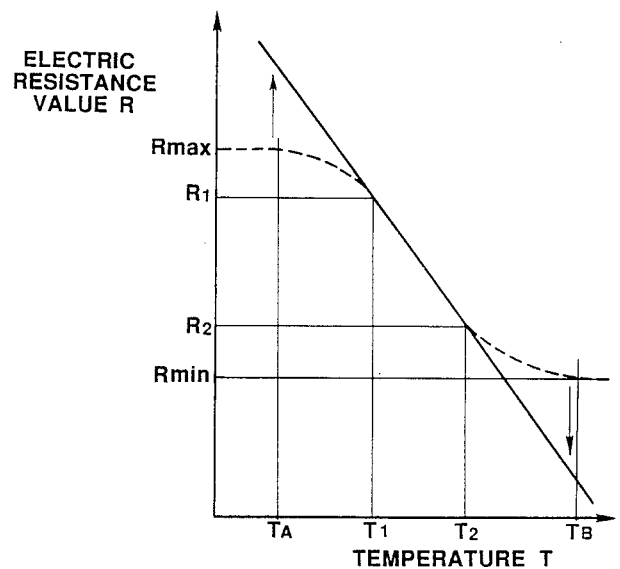

As shown in FIG. 34, the above mentioned resistance value linearly varying part detecting circuit 232 comprises a means of measuring the variation of the electric resistance value of the driving member 228 by the initial electrification, detecting the range in which the resistance value varies linearly as shown as $R_1$ to $R_2$ in FIG. 37 and storing it and a means of determining on the basis of this detected result whether the electric resistance value of the driving member 228 when actually driving is in the linearly varying range or not.

The electric resistance value of the driving member 228 detected by the initial electrification is input into a gate circuit 233 arranged within the resistance value linearly varying part detecting circuit 232. Into this gate circuit 233 is input an initial electrification controlling signal from an electrification controlling part 246 as is shown in FIG. 35(a). Also, a current as is shown in FIG. 35(c) is passed through the driving member 228 by an electrifying circuit 247 at the same timing as of the above mentioned initial electrification controlling signal. Only an electric resistance value detecting signal of the driving member 228 in the initial electrifying period as is shown in FIG. 35(c) is output to a differentiating circuit 234 and memorizing part 238 in the later step. In the above mentioned differentiating circuit 234, as shown in FIG. 35(), a differentiating output signal as becomes zero in the period in which the input electric resistance value detecting signal linearly varies is output to a comparing circuit (a) 235. In this comparing circuit (a) 235, in the period in which the input signal becomes zero, a signal as is shown in FIG. 35(e) is output. The period in which the signal is output from the comparing circuit (a) 235 coincides with the period in which the electric resistance value of the driving member 228 varies linearly. Therefore, on the basis of the output signal from the above mentioned comparing circuit (a) 235, a trigger signal as is shown in FIG. 35(f) is output from a trigger signal generating circuit (a) 236 and a resistance value signal with which the electric resistance value of the driving member 228 begins to show a linear variation is stored in the memorizing part 238. Based on the fall of the output signal from the above mentioned comparing circuit (a) 235, a trigger signal as is shown in FIG. 35(g) is output from a trigger signal generating circuit (b) and a resistance value signal to be of a threshold value shifting from the region in which the electric resistance value of the driving member 228 shows a linear variation to the region in which it varies non-linearly is stored in the memorizing part 238.

As described above, the resistance value linearly varying part of the driving member 228 is detected and stored by the initial electrification.

When the driving member 228 is being actually operated, the output of the resistance value detecting part 231 will be compared with the two values showing the resistance value linearly varying part detected and stored by the above described initial electrification in a comparing circuit (b) 239. The output signal of this comparing circuit (b) 239 is input into a logical circuit 240 in which it is determined in which of the linearly varying region (between $R_1$ and $R_2$), the non-linear region (above $R_1$) saturated with the maximum value and the non-linearly varying region (below $R_2$) gradually approaching the minimum resistance value the resistance value of the above mentioned driving member 228 is located and the signal corresponding to the result is output to a conversion controlling part 241 arranged within the light source apparatus 222 as an output of the resistance value linearly varying part detecting circuit 232.

Figure 33:
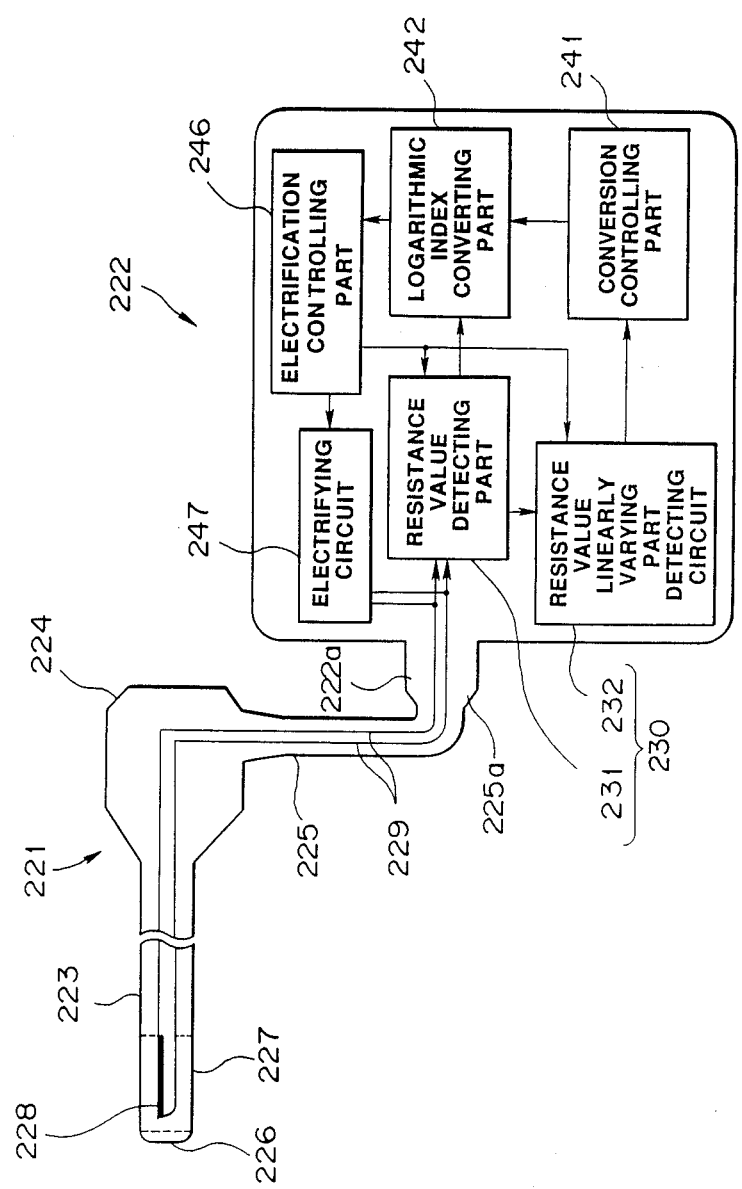
Figure 36:
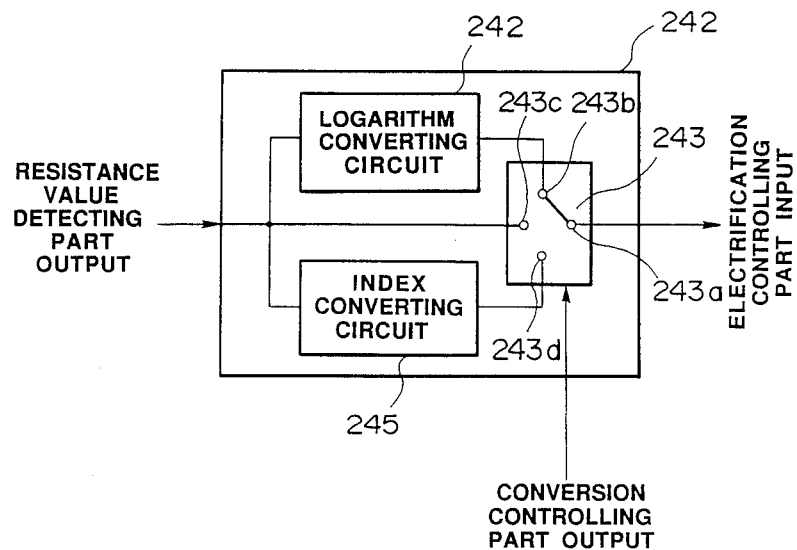

As shown in FIGS. 33 and 36, the above mentioned conversion controlling part 241 is connected to a switching switch 243 arranged within the above mentioned logarithm-index converting part 242 so that the connection among a single output terminal 243a and three input terminals 243b, 243c and 243d provided in this switching switch 243 may be switched by the output from the above mentioned conversion controlling part 241.

While the above mentioned output terminal 243a is connected to an electrification controlling part 246 which is an example of a controlling means provided within the light source apparatus 222, the input terminal 243c arranged in the center of the three input terminals 243b, 243c and 243d is connected to the above mentioned resistance value detecting part 231. A logarithm converting circuit 244 is interposed between the resistance value detecting part 231 and input terminal 243b and an index converting circuit 245 is interposed between the resistance value detecting part 231 and input terminal 243d. In case the input terminal 243b and output terminal 243a are connected with each other, the signal of the output of the above mentioned resistance value detecting part 231 logarithmically converted in the logarithm converting circuit 244 will be input into the electrification controlling part 246. On the other hand, in case the input terminal 2443d and output terminal 243a are connected with each other, the signal of the output of the resistance value detecting part 231 index-converted in the index converting circuit 246 will be input into the electrification controlling part 246. Further, in case the output terminal 243a is connected to the input terminal 243c, the output of the above mentioned resistance value detecting part 231 will be output to the above mentioned electrification controlling part 246 as an output of this logarithm-index converting part 242.

Therefore, when the resistance value of the driving member 228 detected by the above mentioned resistance value detecting part 231 is above $R_1$ shown in FIG. 37, this resistance value will be logarithmically converted, when it is within the range from $R_1$ to $R_2$, the resistance value will not be converted and, when it is below $R_2$, the resistance value will be index-converted.

The above mentioned electrification controlling part 246 into which the output of this logarithm-index converting part 242 is input is connected to an electrifying circuit 247 as an electrifying means connected to the electric wires 229 and the above mentioned resistance value detecting part 231. This electrifying circuit 247 electrifies and heats the above mentioned driving member 228, for example, by a pulse width modulating system through the electric wires 229 by the signal from the above, mentioned electrification controlling part 246. The resistance value detecting part 231 detects the electric resistance value of the driving member 228 during the period of stopping the electrification of the driving member 228 by the signal from, the electrification controlling part 246.

When making an observation or therapy with an endoscope apparatus having such a formation, when the endoscope 221 and light source apparatus 222 are connected with each other through the connector apparatus 225a and the insertable part 223 is inserted into a body cavity or pipe hole, the electrifying circuit 247 will be controlled by the signal from the electrification controlling part 246, the driving member 228 will be electrified through the electric wires 229 by this electrifying circuit 247, then the driving member 228 will be heated and transformed and the curvable part 227 will be curved in response to this transformation.

When the above mentioned driving member 228 is transformed, the electric resistance value of this driving member 228 will vary. This resistance value is detected by the resistance detecting part 231 during the period of stopping the electrification of the driving member 228. This detected result is output to the resistance value linearly varying part detecting circuit 232 and logarithm-index converting circuit 242.

In this resistance value linearly varying part detecting circuit 232, it is determined whether the electric resistance value of the above mentioned driving member 228 is in the non-linear region above $R_1$ saturated with the maximum resistance value, the linearly varying region between $R_1$ and $R_2$ or the non-linear region below $R_2$ gradually approaching the minimum resistance value shown in FIG. 37 and this determined result is output to the conversion controlling part 241.

In this conversion controlling part 241, based on the signal input from the above mentioned resistance value linearly varying part detecting circuit 232, a control signal is produced and is input into the logarithm-index converting part 242 so that the output terminal 243a and input terminals 243b, 243c and 243d of the switching switch 243 of the logarithm-index converting part 242 may be switched to be in a proper combination.

When the electric resistance value of the above mentioned driving member 228 is above $R_1$ shown in FIG. 37, the output terminal 243a will be connected to the input terminal 243b so that the signal detected in the resistance value detecting part 231 as logarithmically converted may be input into the electrification controlling part 246 as an output of the converting part 242. When the electric resistance value of the driving member 228 is between $R_1$ and $R_2$, the central input terminal 243c and output terminal 243a will be connected with each other and the detected result itself in the resistance value detecting part 231 will be input into the electrification controlling part 246. When the electric resistance value is below $R_2$, if the output terminal 243a is connected to the input terminal 243d, the result detected in the resistance value detecting part 231 as index-converted will be input into the electrification controlling part 246 as an output of the converting part 242.

Even if the electric resistance value for the temperature of the above mentioned driving part 228 has such a characteristic as is shown by the broken lines in FIG. 37, as shown by the solid line in the same diagram, the non-linear region will be converted to a linearly varying resistance value which will be input into the electrification controlling part 246.

When the electrifying circuit 247 is controlled by the electrification controlling part 246 based on this input resistance value, the amount the electrification to the above mentioned driving member 228 will be controlled.

Therefore, not only when the electric resistance value of the driving member 228 is in the linearly varying region but also when it is in the non-linear region, this driving member 228 will be able to be correctly controlled and the curvature of the curvable part 227 will be able to be set to be large.

The actual used range in this case is the temperature range ($T_A$ to $T_B$) reached by R min from R max as shown in FIG. 37 and, outside this range, the heating or cooling will be stopped.

The shape of the above mentioned driving member 228 may be not only band-like but also, for example, like a plate or coil. This driving member may be formed of not only a shape memorizing alloy but also other material such as a shape memorizing plastic pasted with a heating coil.

The above mentioned driving member 228 may be not only built-in in the curvable part 227 but also provided outside.

In this embodiment, the resistance value sensing means 230 and controlling means 246 have been explained to be arranged within the light source apparatus 222 but are not limited to this example and may be formed as another apparatus separately from the light source apparatus.

Figure 38:
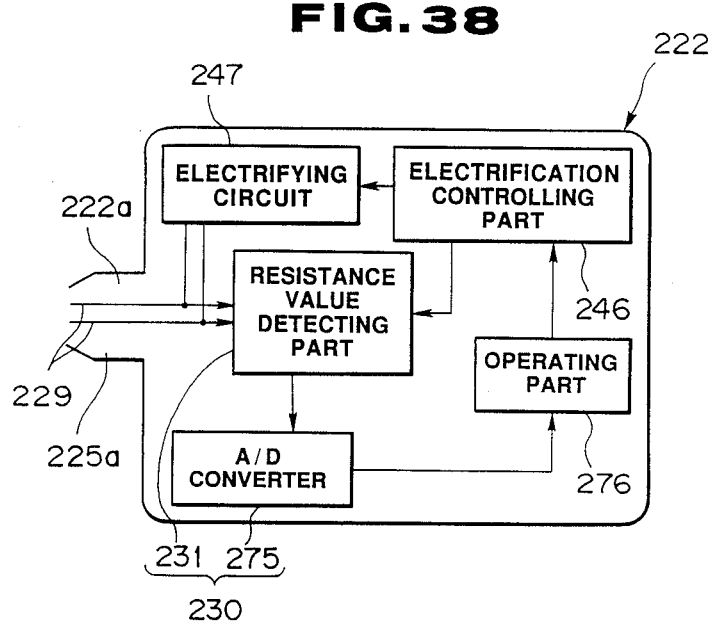
FIGS. 38 and 39 relate to the 13th embodiment of the present invention.
Figure 39:
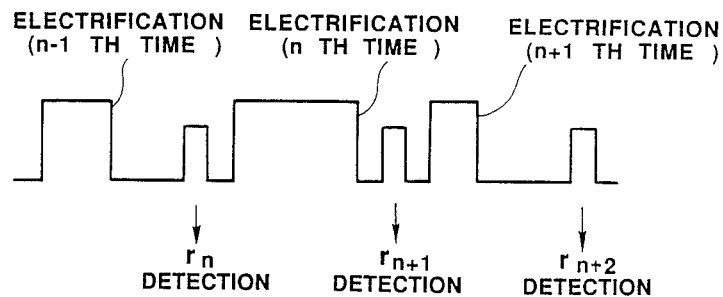

FIGS. 38 and 39 show the 13th embodiment of the present invention. The same members and the members having the same operations as in the 12th embodiment shall bear the same reference numerals and shall not be explained here.

In this embodiment, instead of the resistance value linearly varying part detecting circuit 232 explained in the 12th embodiment, an A/D converter 275 is connected to the resistance value detecting part 231 and, instead of the logarithm-index converting circuit 242, an operating part 276 is interposed between the above mentioned A/D converter 275 and electrification controlling part 246.

While a driving member (not illustrated) is electrified by a pulse modulating system from the electrifying circuit 247, during the electrification stopping period, the electric resistance value of this driving member is detected by the resistance value detecting part 231. The detected result is sampled as $R_n$, $R_{n+1}$, $R_{n+2}$, ... by the A/D converter 275 and is output to the operating part 276.

In this operating part 276, based on the sampled resistance value, $$\Delta a = R_{n+1} - R_n,$$
$$\Delta b = R_{n+2} - R_{n+1},$$
$$\cdots \quad \cdots$$

are operated to determine the values of $\Delta a$, $\Delta b$, ... ... and, when $\Delta a = \Delta b$, $R_{n+2}$ will be output to the electrification controlling part 246 as an electric resistance value of the above mentioned driving member and, on the other hand, when $\Delta a \neq \Delta b$, the value of $$20 \log \{K/\Delta b - \Delta a)\}R_{n+2}$$

(wherein K is a constant)

will be determined and will be output to the above mentioned electrification controlling part 246.

This operation will be made whenever the resistance value is sampled. As a result, the same as in the explanation in the above described first embodiment, the resistance value of the above mentioned driving member is converted to a resistance value in which the non-linearly varying region varies to be linear.

The electrifying circuit 247 is controlled based on the operated value input into the above mentioned electrification controlling part 246.

The driving member can be correctly controlled even in the non-linearly varying region and the curvature of the curvable part can be set to be large.

This embodiment has been explained to use the A/D converter 275 but, instead of this A/D converter 275, for example, a sample holding circuit may be used to make the same operation.

Figure 40:
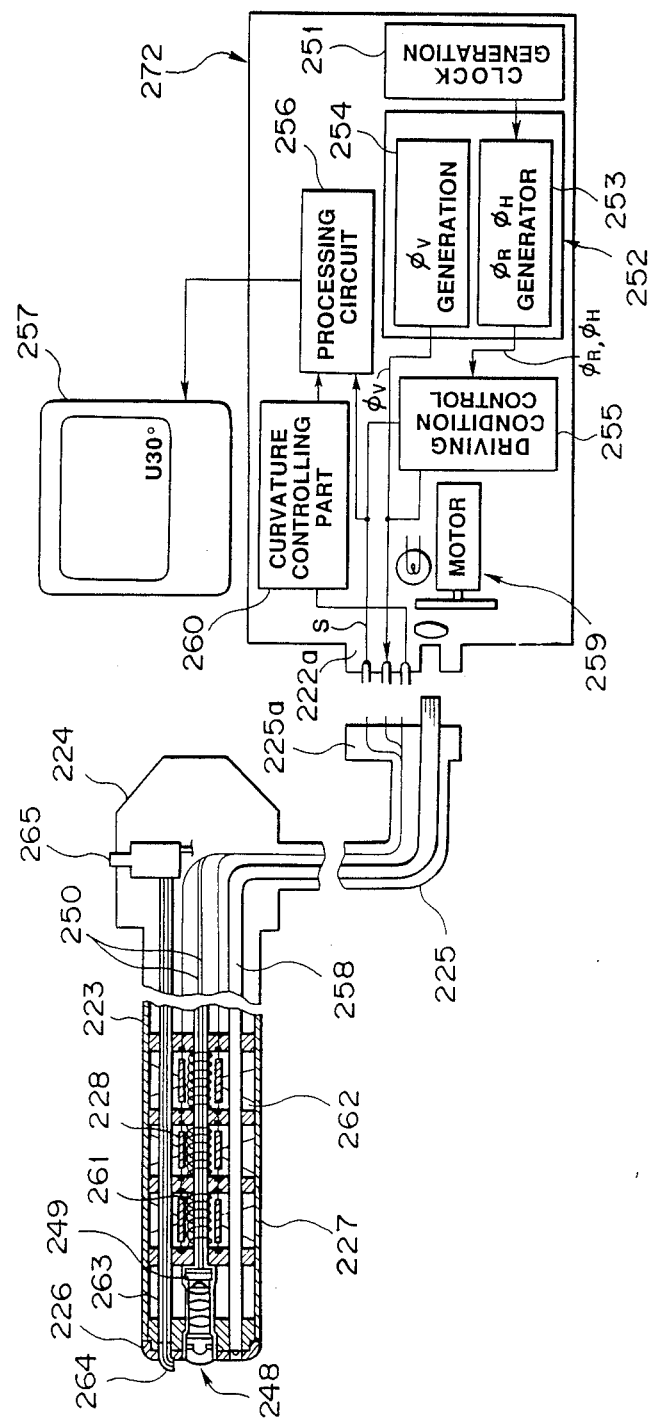
FIG. 40 is a schematic formation diagram of a system relating to the 14th embodiment of the present invention.

FIG. 40 is a schematic formation diagram of a system relating to the 14th embodiment of the present invention.

In this embodiment, an endoscope 221 is formed as a video endoscope, an objective lens 248 forming a video image of a part to be observed is arranged in a tip part 226 provided on the tip side of an insertable part 223 and a CCD 249 is fixed in the focus position of this objective lens 248.

Signal wires 250 are connected at one end to this CCD 249 and are fixed at the other end to a connector apparatus 225a provided at the tip of a universal cord 225 extended out of one side of an operating part 224 through this universal cord and are connected to a camera controlling unit (CCU) 272 or video processor through the connector apparatus 225a.

A clock signal generator 251 and driving circuit 252 are provided within this CCU so that, when a clock signal generated by the clock signal generator 251 is input into this driving circuit 252, a driving signal for the above mentioned CCD 249 may be produced and may be output to the CCD 249 through the above mentioned signal wires 250. A reset horizontally transferred pulse generator 253 and vertically transferred pulse generator 254 are provided within the above mentioned driving circuit 252 to generate respectively a reset pulse $\Phi H$ and vertically transferred pulse $\Phi V$.

While the above mentioned vertically transferred pulse $\Phi V$ is applied to the above mentioned CCD 249 through the signal wires 250, the reset horizontally transferred pulse $\Phi R$ and horizontally transferred pulse $\Phi H$ are applied to the above mentioned CCD 249 through a driving condition controlling circuit 255.

When a driving signal from the above mentioned driving circuit 252 is applied, the above mentioned CCD 249 will input a photoelectrically converted signal into the above mentioned driving condition controlling circuit 255 through the signal wires 250 and also into a processing circuit 256 provided within the above mentioned CCD 272 and the processing circuit 256 will take in and process this signal to be video signal and will output it to a monitor 257.

Also, a light guide 258 transmitting an illuminating light is arranged within the above mentioned insertable part 223 and is fixed at one end to an illuminating through hole of the above mentioned tip part 226 and at the other end to the above mentioned connector apparatus 225a so that an illuminating light from a light source part 259 provided within the CCD 272 may be transmitted to the above mentioned tip part and may be radiated to a part to be observed.

In this embodiment, a curvable part 227 provided on the base end side of the above mentioned tip part 226 is formed of a plurality of curvable frames 262 rotatably connected with one another. A driving member 228 formed, for example, of a shape memorizing alloy is built-in in the above mentioned curvable part 227 so that, by shrinking this driving member 228 in the axial direction, the above mentioned curvable frame 262 may be rotated to curve the curvable part 227. The driving member 228 is connected to a curvature controlling part 260 provided within the above mentioned CCU 272 through the signal wires 250. A bias spring 261 energizing this curvable part 227 to be linear is provided in the center of the above mentioned curvable part 227.

This curvature controlling part 260 is formed the same as in the essential part of the light source apparatus explained in the above described 12th or 13th embodiment so that an electrification controlling part (not illustrated) may calculate the curvature from the objective curving angle or the resistance value of the driving member 228 detected by the resistance value detecting part and may output it to the above mentioned processing circuit 256 and, when the above mentioned curvable part 7 is curved, for example, by 30 degrees upward, it may be displayed as U 30° on the picture surface of the above mentioned monitor 257.

An air and water feeding nozzle 264 is provided in the tip part 226 and an air and water feeding channel 263 communicating with the above mentioned air and water feeding nozzle 264 is provided within the insertable part 223 and universal cord 225. An air and water feeding button 265 interposed in the course of the above mentioned air and water feeding channel 263 is provided in the operating part 224.

According to such a formation, as the curved state and curving angle of the curvable part 227 are displayed on the picture surface, there is an effect that the operatability is high.

FIGS. 41 to 46 show the 15th embodiment of the present invention.

In this embodiment, the present invention is applied to a catheter.

Figure 41:
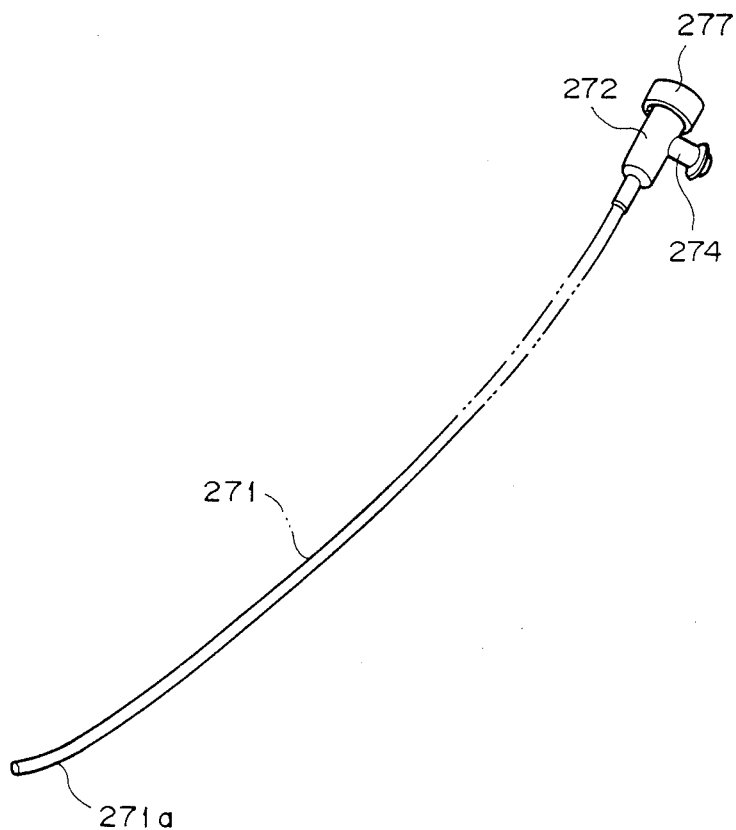
FIGS. 41 to 46 relate to the 15th embodiment of the present invention.

In FIG. 41, the reference numeral 271 represents a tube formed of a synthetic resin doing no harm and low in the friction coefficient as, for example, polyamide, ethylene tetrafluoride or a copolymer of ethylene tetrafluoride and propylene hexafluoride. A cylindrical mouthpiece 272 is coaxially fitted and fixed to the tube 271 at the base end. An injecting port part 274 having an injecting hole 273 communicating with the above mentioned tube 1 through the hollow part within the mouthpiece 272 is provided on the side of this mouthpiece 272. A grip 277 of a core body 276 can be removably fitted to an opening part 275 at the rear end of the mouthpiece 272. The above mentioned core body 276 is made, for example, of a synthetic resin comparatively high in the rigidity and has the above mentioned grip 277 bonded and fixed to the rear end. The core body 276 is inserted into the tube 271 through the mouthpiece 272. A clearance large enough to flow an image forming agent as described later is formed between the core body 276 and the inside surface of the tube 271. The core body 276 is set to be of a length reaching the vicinity of the rear end of the tip part 271a without thrusting at the tip through the tube 271. As the core body 276 is not positioned within the tip part 271a of the tube 271, the tip part 271a can be easily and freely bent and has a bending habit as bent.

Figure 42:
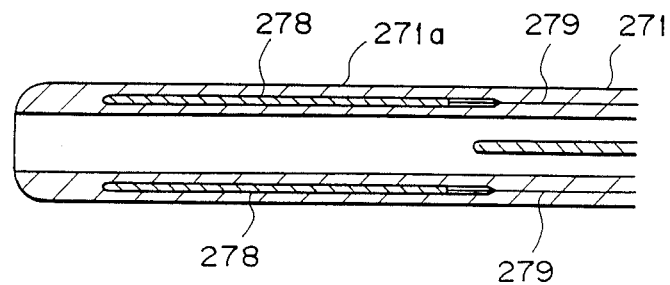
Figure 43:
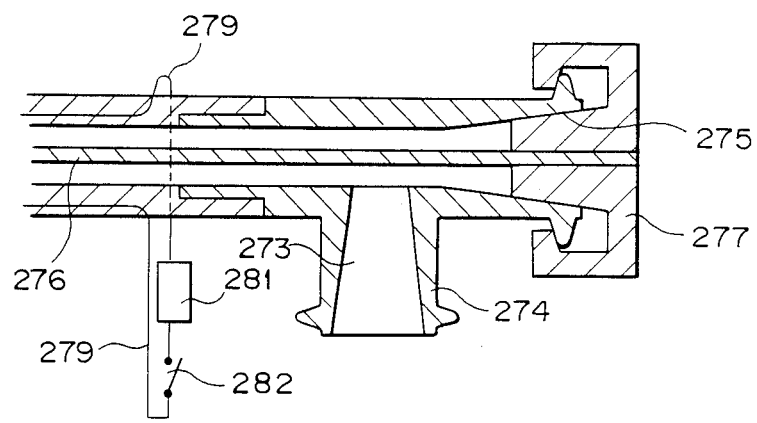

Further, a plurality of energizable members 278 formed to be linear as shown in FIG. 42 are embedded in the lengthwise direction within the thickness of the tip part 271a of the tube 271 and are formed of a shape memorizing alloy as, for example, a Cu-Zn-Al alloy or Ti-Ni alloy. This energizable member 278 will become straight when the shape memorizing alloy is of a mother phase (high temperature phase) and will be energized to be linear even if bent in the tip part 271a. Further, when it is plastically transformed by applying an external force at the normal temperature (body temperature), it will cause a martensite transformation to form a martensite phase. There is used an energizable member in which the temperature Af at which the reverse transformation from the martensite phase to the mother phase ends is above the body temperature or is, for example, 50°C.

On the other hand, lead wires 279 are connected to the energizable members 278 embedded within the thickness of the tip part 271a so that an electric current may flow over the entire length, are led to the rear end part of the tube 271 through the thickness of the tube 271, are then led out and are connected to a driving circuit in an external current source circuit so that the energizable members 278 may be fed with an electric current through the above mentioned lead wires 279 and may be heated with Joule heat (resistance heat).

The above mentioned driving part 281 comprises the resistance detecting part 3, comparator 4, controller 6, driving part 7 and controlling part 8 shown in FIG. 1 of the first embodiment and controlling to control the curvature of the energizable members 278 the same as in the first embodiment. The using manner of the above mentioned embodiment shall be explained in the following with reference to FIGS. 44 to 46.

Figure 44:
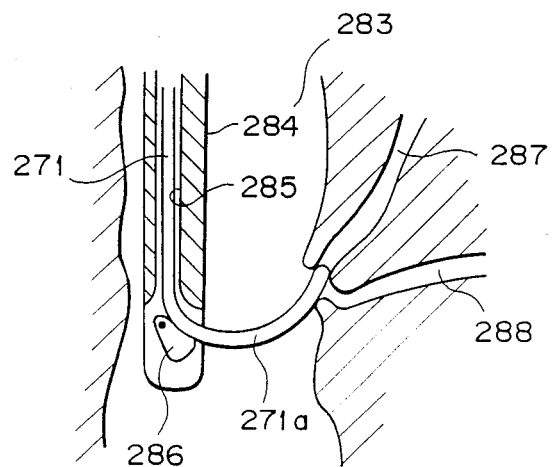
Figure 45:
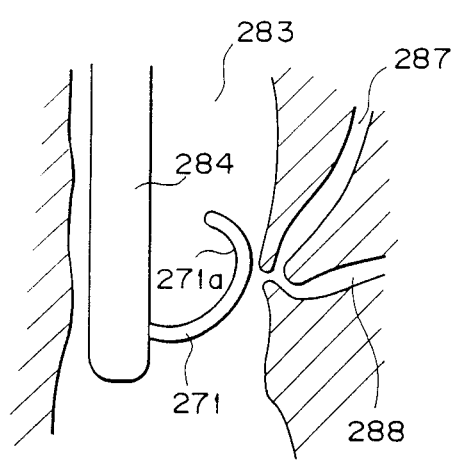
Figure 46:
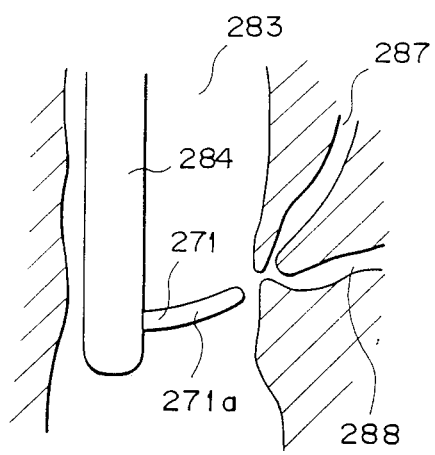

First of all, the tube 271 is led out into the duodenum descending leg 293 through the inserting channel 285 of the endoscope 284 led into the duodenum descending leg 283. The energizable members 278 on one side are heated by electrification and heating to be bent in the running direction of the bile duct 287. Then, as shown in FIG. 44, the tip part 271a of the tube 271 is inserted into the bile duct 287 in the running direction of the bile duct 278. However, the opening part of the bile duct 287 is so narrow that the running direction of the bile duct 287 can not be known definitely and therefore the bend of the tip part 271a is not likely to coincide with the running direction of the bile duct 287. In such case, it will be very difficult to insert it aS it is. Therefore when the bending degree is small, it may be increased but, when the bending is too large, the energizable members 278 on the other side made of a shape memorizing alloy may be fed with an electric current through the lead wires 279 by the driving circuit 281 of the external current source circuit so as to be heated by Joule heat. Then, by applying a proper curvature, the tip part 271a may be inserted into the bile duct 287. When it is positively inserted, an injector or the like (not illustrated) may be connected to the injecting port part 275 to press in an image forming agent.

After the image forming agent is injected into the bile duct 287, in case the image forming agent is to be injected also into the pancreatic duct 288, with the tube 271 inserted through the inserting channel 285 of the endoscope 284 as it is, the energizable members 278 may be fed with an electric current by the driving circuit 281 of the external current source circuit so as to be heated the same as in the above. By applying a proper curvature, the tip part 271a may be inserted into the pancreatic duct 288.

Figure 47:
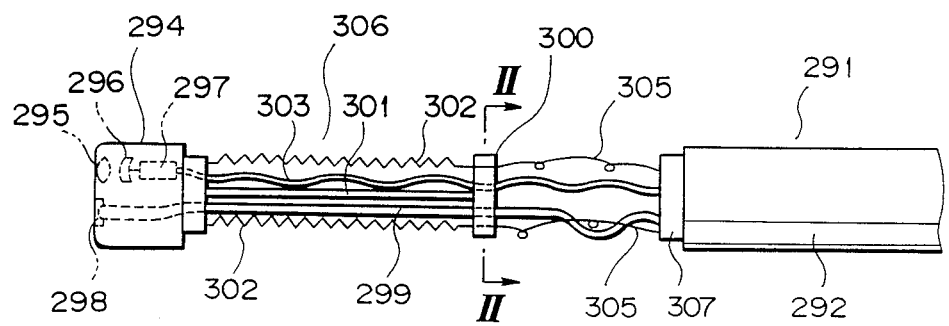
FIGS. 47 to 49 show the 16th embodiment of the present invention.
Figure 48:
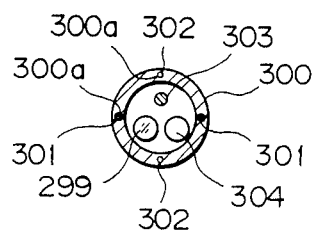
Figure 49:
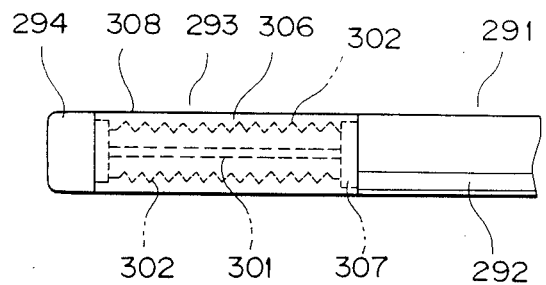

FIGS. 47 to 49 show the 16th embodiment of the present invention.

In this embodiment, a curvable unit mode of a shape memorizing member can be removably connected to a flexible tube of an insertable part.

FIG. 49 shows a tip part of an insertable part 291 of an endoscope to be inserted into a body cavity. This insertable part 291 comprises an elongate flexible tube 292, a curvable part 293 formed on the tip side of this flexible tube 292 and a tip forming part 294. As shown in FIG. 47, an objective optical system 295, a solid state imaging device 296 consisting of a CCD, a driving circuit 297 for driving it, an illuminating optical system 298 and a tip part of a light guide fiber 299 are built-in in this insertable part 291. A ring-like fixing member 300 is provided as separated by a predetermined distance in the rear of the tip forming part 294. These tip forming part 294 and fixing member 300 are connected with each other through a pair of flexible shafts 301 in the positions opposed to each other on the periphery in the horizontal direction as shown in FIG. 48.

Further, a pair of driving bodies 302 made of an SMA are arranged in the positions opposed to each other on the periphery in the vertical direction intersecting at right angles with the horizontal direction of the above mentioned flexible shafts 301 between the tip forming part 294 and fixing member 300, are inserted and fixed at one end in holes (not illustrated) formed on the end surface of the tip forming part 294 and are inserted and fixed at the other end in holes 300a formed on the end surface of the fixing member 300. When fixing the driving bodies 302 directly to the fixing member 300, the fixing member 300 will be formed of an electrically insulating material such as a resin or ceramics and, when forming the fixing member 300 of an electric conductive material such as stainless steel or aluminum, the driving bodies 302 will be coated at the ends with an insulating material such as ceramics and then will be fixed to the fixing member 300.

The driving bodies are made of a Ti-Ni alloy or Cu-Zn-Al alloy, vary in the structure at the temperatures above and below a predetermined transformation temperature (depending on the alloy used therefor and its composition rate and the like) as a boundary and have a shape storing action memorizing the shape of the structure on the high temperature side above the above mentioned transformation temperature so that, when the high temperature side shape is worked in advance, by heating above the transformation temperature, the shape will be transformed to the original memorized shape. In this case, a closely contacted coil shape is stored in advance in the driving bodies 302 so that, when they are fitted, the coil shape will be extended. The driving bodies 302 are arranged vertical direction but may be arranged also in the horizontal direction. The transformation temperature (austenite transformation finishing temperature Af) to the mother phase is properly set at a temperature higher than the body temperature, that is, in a range of 40° to 90° C.

A cable 303 connected to the above mentioned driving circuit 297, the light guide fiber 299 and a treating instrument inserting channel 304 are inserted through the above mentioned fixing member 300. Lead wires 305 for electrifying and heating the above mentioned driving bodies 302 are inserted and fixed as connected to the rear ends of the driving bodies 302 on the rear end surface of the fixing member 300. Though not illustrated, heating lead wires are connected also to the tips of the driving bodies 302. These lead wires 305 are connected to an external electrifying apparatus (not illustrated) through the flexible tube 292 and the operating part (not illustrated) on the hand base side.

An integral curvable unit 306 is formed of the tip forming part 294, fixing member 300, flexible shaft 301 and driving bodies 302. When the fixing member 300 of this curvable unit 306 is inserted into the ring-like mouthpiece 307 provided at the tip of the flexible tube 292 and then these fixing member 300 and mouthpiece 307 are fixed with screws or the like, the curvable unit 306 will be removably connected to the flexible tube 292. When the curvable unit 306 is thus connected to the flexible tube 292 and, as shown in FIG. 49, the part between the tip forming part 294 and flexible tube 292, that is, the curvable unit 306 except the tip forming part 294 is coated on the outer periphery with a flexible outer cover such as is made of a rubber tube, the insertable part 291 will be assembled.

In the endoscope of this formation, usually (when the driving bodies are not being electrified), the curvable part 303 is kept straight by the elasticity of the flexible shaft 301. In this state, when the driving body 302 on one side is electrified and heated with Joule heat through the lead wires 305, above the transformation temperature, the driving body 302 will shrink in the axial direction to be of the original memorized shape (closely contacted coil shape) against the elasticity of the flexible shaft 301. The curvable part 293 will curve to be arcuate on one side with respect to the center axis so as to be able to be curved in any desired direction. At this time, when the amount of electrification to the driving body 303 on one side is properly controlled, the curvature of the curvable part 293 will be able to be controlled. In case the curvable part 293 is to be straight, if the electrification of the driving body 302 is stopped and the driving body 302 is kept below the transformation temperature, the driving body 302 will be stretched by the returning force of the flexible shaft 301 and the curvable part 293 will be able to be straight. On the other hand, in case the curvable part 293 is to be curved on the other side, the driving body 302 on the other side may be electrified and heated.

As the driving bodies 302 made of an SMA are not fixed directly to the insertable part 291 but are incorporated in the curvable unit 306 so as to be removable from the flexible tube 292, before the curvable unit 306 is perfectly assembled to the flexible tube 292, with the curvable unit 306 alone, the operation can be easily confirmed as by electrifying and heating the respective driving bodies 302. In case the driving body 302 is broken or permanently deformed, as shown in FIG. 47, the curvable unit 306 may be slipped forward and removed from the flexible tube 292 to expose the driving body 302 which can be easily replaced. At the time of assembling the driving bodies 302, it will be necessary to adjust the amount of their stretch. In a case, too, with the curvable unit alone, the driving bodies 302 will be able to be assembled while seeing the curvature with the electrification and heating.

Figure 50:
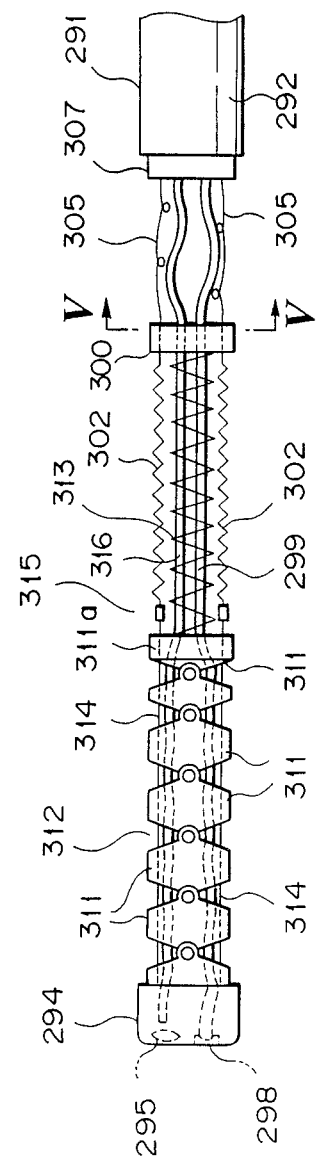
FIGS. 50 to 52 show the 17th embodiment of the present invention.
Figure 52:
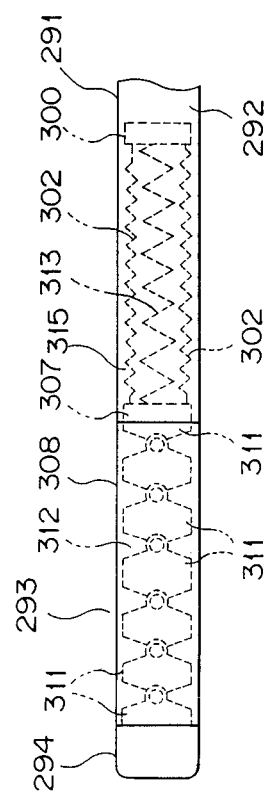
Figure 51:
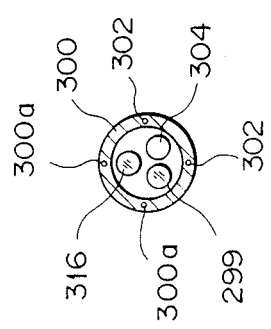

FIGS. 50 to 52 show the 17th embodiment of the present invention.

With this embodiment, a curvable part 293 is formed of a flexible tube 312 made by linearly pivoting many curvature frames 311 in the rear of a tip forming part 294. A ring part 311a is formed on the curvature frame 311 at the last end of this curvable tube 312. This ring part 311a and a fixing member 300 are connected with each other by a coil spring 313. Within the curvable tube 312, four operating wires 314 are inserted at intervals of 90 degrees corresponding to the curving directions, are fixed respectively at one end to the tip forming part 294 and are led at the other ends out of the curvable tube 312 and connected by soldering or the like with the same driving bodies 302 as in the above mentioned 17th embodiment respectively at one end. The respective driving bodies 302 are fixed at the other ends to the fixing member 300. In this case, an integral curvable unit 315 is formed of the tip forming part 294, curvable tube 312, operating wires 314, fixing member 300, coil spring 313 and driving bodies 302 and, after this curvable unit 315 is inserted in the part in the rear of the curvable tube 312 into the flexible tube 292, when the ring part 311a at the rear end of the curvable tube 31 and the mouthpiece 307 at the tip of the flexible tube 292 are fixed with screws or the like, the curvable unit 315 will be removably connected to the flexible tube 292. After the curvable unit 315 is connected to the flexible tube 292, the part between the tip forming part 294 and flexible tube 292, that is, the curvable tube 312 is coated on the outer periphery with a flexible outer cover 308 made of a rubber tube or the like to assemble the insertable part 291. The reference numeral 316 represents an image guide fiber. The other basic formations are the same as in the above mentioned 17th embodiment.

When the driving body 302 is electrified and heated to be shrunk, the operating wire 314 will be pulled and the curvable part 293 will be curved on the pulled side. When the electrification of the driving body 302 is stopped, the driving body 302 will be returned to be stretched by the returning force of the coil spring 313 and the curvable part 293 will become straight.

Even in such a formation, as the driving bodies 302 are incorporated in the curvable unit 315 so as to be unified, there are the same effects as in the above mentioned 17th embodiment.

Figure 53:
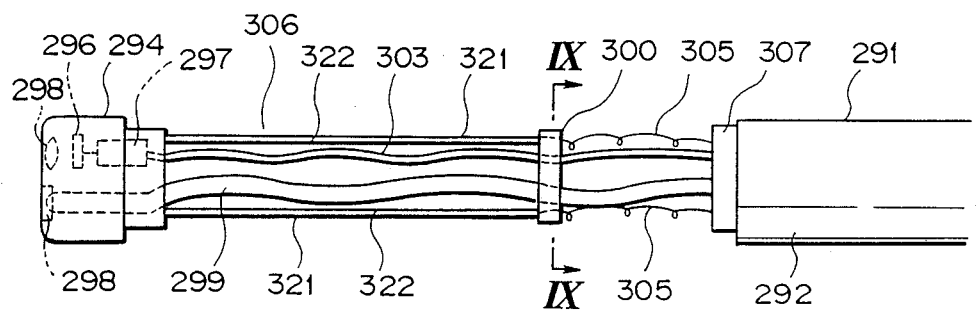
FIGS. 53 to 55 show the 18th embodiment of the present invention.
Figure 54:
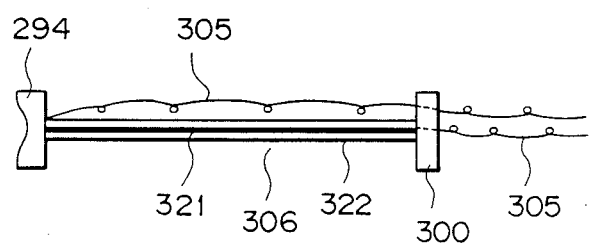
Figure 55:
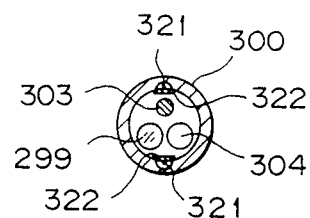

FIGS. 53 to 55 show the 18th embodiment of the present invention.

With this embodiment, four driving bodies 321 are made of the same material as in the above mentioned 16th embodiment but are formed to be like wires and four plate-like springs 322 are used in place of the flexible shaft 301 and coil spring 313 in the 16th and 17th embodiments. The driving bodies 321 are made to store a linear shape in advance so as to be stretched when fitted. Other basic formations are the same as in the above mentioned 16th embodiment.

When the driving body 321 is electrified and heated to be shrunk, the curvable part 293 will be curved on the shrunk side. When the electrification of the driving body 321 is stopped, the driving body 321 will be stretched by the returning force of the plate spring 322 and the curvable part 293 will become straight.

Even in such a formation, the same effects as in the above mentioned 16th embodiment are obtained.

The shapes of the driving bodies 302 and 321 may be plate-like.

We claim:

1. A position controlling apparatus comprising:
   an actuator having a shape monitoring alloy body as a power source;
   a driving means for heating or cooling said shape memorizing alloy body and for displacing said actuator by heating or cooling;
   a comparing means for outputting a difference between actual displacement of said actuator driven by said driving means and objective displacement of said actuator and for operating said driving means on the basis of said difference;
   a resistance value detecting means for detecting the resistance value of said shape memorizing alloy body varying when said shape memorizing alloy body is heated or cooled; and
   a controlling means for inputting the detected resistance value detected by said resistance value detecting means and for controlling said driving means based on said detected resistance value and a preset value of a temperature range of said shape memorizing alloy body.

2. A position controlling apparatus according to claim 1 wherein said controlling means will have said driving means stop heating or cooling said shape memorizing alloy body when the temperature of said shape memorizing alloy body is outside the temperature range of said shape memorizing alloy body.

3. A position controlling apparatus according to claim 2 wherein said controlling means comprises:
   a displacement calculating means for calculating a normalized resistance value from the resistance value from said resistance value detecting means, a resistance value R min on a high temperature side of said preset temperature range and a resistance value R max on a low temperature side of said temperature range and for outputting said normalized resistance value to said comparing means;
   a memorizing part storing said resistance value R min and resistance value R max; and
   a controller which inputs the resistance values R min and R max stored in said memorizing part and the resistance value from said resistance value detecting means and will have said driving means stop heating or cooling said shape memorizing alloy body when the resistance value is outside the range of the resistance value R min and resistance value R max.

4. A position controlling apparatus according to claim 1 wherein said controlling means comprises:
   a displacement calculating means for calculating a normalized resistance value from the resistance value from said resistance value detecting means, a resistance value R min on a high temperature side of said preset temperature range and a resistance value R max on a low temperature side of said temperature range and for outputting said normalized resistance value to said comparing means; and
   a memorizing part storing said resistance value R max and resistance value R min.

5. A position controlling apparatus according to any of claims 3 or 4 wherein said memorizing part renews the resistance value R max and resistance value R min before position control of said actuator starts.

6. A position controlling apparatus according to claim 4 wherein said controlling means further comprises a position sensor which can detect a displaced position of said actuator.

7. A position controlling apparatus according to claim 4 wherein said controlling means further comprises a force sensor detecting a force produced by displacement of said actuator.

8. A position controlling apparatus according to claim 1 further comprising a converting means for logarithm or index-converting a non-linearly varying resistance value detected by said resistance value detecting means to a linearly varying resistance value.

9. A position controlling apparatus comprising:
   an actuator having a shape memorizing alloy body as a power source;
   a driving means for heating or cooling said shape memorizing alloy body and for displacing said actuator by said heating or cooling;
   a comparing means for outputting a difference between an actual displacement of said actuator driven by said driving means and an objective displacement of said actuator and for operating said driving means based on said difference;
   a resistance value detecting means for detecting a resistance value of said shape memorizing alloy body varying when said shape memorizing alloy body is heated or cooled;
   a displacement calculating means for calculating a normalized resistance value from the resistance value from said resistance value detecting means, a resistance value R min on a high temperature side of a preset temperature range and a resistance value R max on a low temperature side of said temperature range and for outputting said normalized resistance value to said comparing means; and
   a memorizing part updated and storing said maximum resistance value R max and minimum resistance value R min before position control of said actuator starts.

10. An endoscope apparatus comprising:
    an endoscope having an insertable part to be inserted into an object to be inspected, an operating part provided at a rear end of said insertable part and a curvable part provided in said insertable part and directing said insertable part tip in at least one direction;
    an actuator provided in said curvable part and having a shape memorizing alloy body as a power source for curving said curvable part;
    a driving means for heating and cooling said shape memorizing alloy body and for displacing said actuator by said heating and cooling;
    a comparing means for outputting a difference between an actual displacement of said actuator driven by said driving means and an objective displacement of said actuator and for operating said driving means based on said difference;
    a resistance value detecting means for detecting a resistance value of said shape memorizing alloy body varying when said shape memorizing alloy body is heated or cooled; and a controlling means for inputting a detected value detected by said resistance value detecting means and for controlling said driving means based on said resistance value and a preset value of a temperature range of said shape memorizing alloy body 11. An endoscope apparatus according to claim 10 wherein said controlling means will have said driving means stop heating or cooling said shape memorizing alloy body when the temperature of said shape memorizing alloy body is outside the temperature range of said shape memorizing alloy body.

12. An endoscope apparatus according to claim 11 wherein said controlling means comprises:
   a displacement calculating means for calculating a normalized resistance value from the resistance value from said resistance value detecting means, a resistance value R min on a high temperature side of said temperature range and a resistance value R max on a low temperature side of said temperature range and for outputting said normalized resistance value to said comparing means;
   a memorizing part storing said resistance value R max and resistance value R min; and
   a controller inputting the resistance values R max and R min stored in said memorizing part and having said driving means stop heating or cooling said shape memorizing alloy body when the resistance value is outside a range of the resistance value R max and resistance value R min.

13. An endoscope apparatus according to claim 10 wherein said controlling means comprises:
   a displacement calculating means for calculating a normalized resistance value from the resistance value from said resistance value detecting means, a resistance value R min on a high temperature side of said temperature range and a resistance value R max on a low temperature side of said temperature range and for outputting said normalized resistance value to said comparing means; and
   a memorizing part storing said resistance value R max and resistance value R min.

14. A position controlling apparatus according to any of claims 12 or 13 wherein said memorizing part updates said resistance value R max and resistance value R min before position control of said actuator starts.

15. An endoscope apparatus according to claim 10 further comprising a converting means for logarithmic or index-converting a non-linearly varying resistance value detected by said resistance value detecting means to a linearly varying resistance value.

16. An endoscope comprising:
   an endoscope having an insertable part to be inserted into an object to be inspected, an operating part provided at a rear end of said insertable part and a curvable part provided in said insertable part and directing said insertable part tip in at least one direction;
   an actuator provided in said curved part and having a shape memorizing alloy body as a power source curving said curvable part;
   a driving means for heating or cooling said shape memorizing alloy body and for displacing said actuator by said heating or cooling;
   a comparing means for outputting a difference between an actual displacement of said actuator driven by said driving means and an objective displacement of said actuator and for operating said driving means based on said difference;
   a resistance value detecting means for detecting a resistance value of said shape memorizing alloy body varying when said shape memorizing alloy body is heated or cooled;
   a displacement calculating means for calculating a normalized resistance value from the resistance value from said resistance value detecting means, a resistance value R min on a high temperature side of a temperature range and resistance value R max on a low temperature side of said temperature range and for outputting said normalized resistance value to said comparing means; and
   a memorizing part updating said resistance value R max and resistance value R min before position control of said actuator starts.

17. An endoscope apparatus according to claim 10 wherein said curvable part is removably connected to said insertable part.

18. An endoscope apparatus according to claim 10 wherein a plurality of said curvable parts are provided in said insertable part.

19. An endoscope apparatus according to any of claims 10 or 16 wherein said controlling means further comprises (a) an operating part inputting said resistance values R max and R min from aid memorizing part and comparing a difference between these resistance values R max and R min with a preset resistance value and (b) a warning means for warning when the difference is smaller than the preset resistance value in the operating part.

20. A catheter apparatus comprising:
   a catheter to be inserted into a body cavity;
   an actuator having a shape memorizing alloy body as a power source curving said catheter at a tip:
   a driving means for heating or cooling said shape memorizing alloy body and for displacing said actuator by said heating or cooling;
   a comparison means for outputting a difference between an actual displacement of said actuator driven by said driving means and an objective displacement of said actuator and for operating said driving means based on said difference;
   a resistance value detecting means for detecting a resistance value of said shape memorizing alloy body varying when said shape memorizing alloy body is heated or cooled; and
   a controlling means for inputting the resistance value detected by said resistance value detecting means and for controlling said driving means based on said resistance value and a preset temperature range of said shape memorizing alloy body.

21. A catheter apparatus according to claim 20 wherein said controlling means will have said driving means stop heating or cooling said shape memorizing alloy body when a the temperature of said shape memorizing alloy body is outside the temperature range of said shape memorizing alloy body.

22. An apparatus according to claim 21 wherein said controlling means comprises:
   a displacement calculating means for calculating a normalized resistance value from the resistance value from said resistance value detecting means, a resistance value R min on a high temperature side of said preset temperature range and a resistance value R max on a low temperature side of said temperature range and for outputting said normalized resistance value to said comparing means;
a memorizing part storing said resistant value R max and resistance value R min; and
a controller inputting the resistance values R max and R min stored in said memorizing part and the resistance value from said resistance value detecting means and having said driving means stop heating or cooling said shape memorizing alloy body when the resistance value is outside a range of the resistance value R min and resistance value R max.

23. A catheter apparatus according to claim 20 wherein said controlling means comprises:
a displacement calculating means for calculating a normalized resistance value from the resistance value from said resistance value detecting means, a resistance value R min on a high temperature side of said preset temperature range and a resistance value R max on a low temperature side of said temperature range and for outputting said normalized resistance value to said comparing means; and
a memorizing means for storing said resistance value R max and resistance value R min.

24. A catheter apparatus according to any of claims 22 or 23 wherein said memorizing part update the resistance value R max and resistance value R min before position control of said actuator starts.

25. A catheter apparatus comprising:
a catheter to be inserted into a body cavity;
an actuator having a shape memorizing alloy body as a power source for curving said catheter at a tip;
a driving means for heating or cooling said shape memorizing alloy body and for displacing said actuator by said heating or cooling;
a comparing means for outputting a difference between an actual displacement of said actuator driven by said driven means and an objective displacement of said actuator and for operating said driving means based on said difference;
a resistance value detecting means for detecting a resistance value of said shape memorizing alloy body varying when said shape memorizing alloy body is heated or cooled;
a displacement calculating means for calculating a normalized resistance value from the resistance value from said resistance value detecting means, a resistance value R min on a high temperature side of a preset temperature range and a resistance value R max on a low temperature side of said preset temperature range and for outputting said normalized resistance value to said comparing means; and
a memorizing part updating and storing acid resistance value R max and resistance value R min before position control of said actuator starts.

26. A position controlling apparatus comprising:
an actuator having a shape memorizing alloy body as a power source;
a driving means for heating said shape memorizing alloy body and for displacing said actuator by said heating;
a comparing means for outputting a difference between an actual displacement of said actuator driven by said driving means and an objective displacement of said actuator and for operating said driving means based on said difference;
a resistance value detecting means for detecting a resistance value of said shape memorizing alloy body varying when said shape memorizing alloy body is heated; and
a controlling means for inputting a detected value detected by said resistance value detecting means and for controlling said driving means based on said detected value and a preset value of a temperature range of said shape memorizing alloy body.

27. A position controlling apparatus according to claim 26 wherein said resistance value detecting means includes a temperature sensor sensing a temperature of said shape memorizing alloy body.

28. A position controlling apparatus according to claim 26 wherein said controlling means includes a displacement calculating means for calculating a normalized resistance value from the resistance value from said resistance value detecting means and R min based on the resistance value on a high temperature side of the for temperature range and outputting said normalized resistance value to said comparing means.

29. A position controlling apparatus according to any of claims 26, 27 or 28 wherein said actuator is arranged on a tip side within an endoscope insertable part having a tip and base end and said controlling means controls curvature of the insertable part made by said actuator.

30. A position controlling apparatus according to any of claims 26, 27 or 28 wherein said actuator is arranged within a tube on a tip side of a catheter having a tip and base end and said controlling means controls curvature on the tip side of the catheter made by said actuator.

31. A position controlling apparatus according to claim 28 wherein said controlling means will stop heating said shape memorizing alloy body when the resistance value of said resistance value detecting means becomes lower than R min.

32. A position controlling apparatus according to claim 1 wherein said resistance value detecting means includes a temperature sensor sensing temperature of said shape memorizing alloy body.

33. A position controlling apparatus comprising:
an actuator having a shape memorizing alloy body as a power source;
a driving means for displacing said actuator by heating or cooling said shape memorizing alloy body;
a resistance value detecting means for detecting a resistance value of said shape memorizing alloy body;
a memorizing part storing a set value corresponding to a high temperature side or a low temperature side of a temperature range of said shape memorizing alloy body;
a comparing part comprising a detected value of said resistance value detecting means with said set value; and
a controlling means for stopping heating or cooling said shape memorizing alloy body when said detected value deviates from said set value for a predetermined period.

34. A position controlling apparatus comprising:
a driving means for displacing a shape memorizing alloy body by heating or cooling;
a resistance value detecting means for detecting a resistance value of said shape memorizing alloy body;
a memorizing part storing the resistance value of said shape memorizing alloy body;
a displacement calculating means for calculating a displacement between a set value stored in said memorizing part and a detected value from said resistance value detecting means;

a comparing means for outputting to said driving means a difference between an objective displacement of said actuator and a displacement by said displacement calculating means; and a controlling means for selectively switching the detecting resistance value from said resistance value detecting means to the memorizing part or displacement calculating means.

* * * * *

UNITED STATES PATENT AND TRADEMARK OFFICE
CERTIFICATE OF CORRECTION

PATENT NO. : 4,977,886
DATED : December 18, 1990
INVENTOR(S) : TAKEHANA et al

It is certified that error appears in the above-identified patent and that said Letters Patent is hereby corrected as shown below:

ON TITLE PAGE: Item [30], delete "April 19, 1989" (second occurrence) and insert therefor --August 11, 1989--; delete "June 4, 1989" and insert therefor --April 6, 1989--; delete "August 2, 1989" and insert therefor --February 8, 1989--.

Signed and Sealed this

Eighteenth Day of August, 1992

Attest:

DOUGLAS B. COMER

Attesting Officer

Acting Commissioner of Patents and Trademarks